(12) United States Patent
Romani

(10) Patent No.: US 11,633,160 B2
(45) Date of Patent: Apr. 25, 2023

(54) WEIGHT MANAGEMENT SYSTEM

(71) Applicant: Renato Romani, Leiden (NL)

(72) Inventor: Renato Romani, Leiden (NL)

(*) Notice: Subject to any disclaimer, the term of this patent is extended or adjusted under 35 U.S.C. 154(b) by 89 days.

(21) Appl. No.: 16/062,487

(22) PCT Filed: Dec. 14, 2016

(86) PCT No.: PCT/US2016/066624
§ 371 (c)(1),
(2) Date: Jun. 14, 2018

(87) PCT Pub. No.: WO2017/106320
PCT Pub. Date: Jun. 22, 2017

(65) Prior Publication Data
US 2019/0029602 A1  Jan. 31, 2019

Related U.S. Application Data

(60) Provisional application No. 62/267,459, filed on Dec. 15, 2015.

(51) Int. Cl.
G09B 19/00 (2006.01)
A61B 5/00 (2006.01)
G01G 19/44 (2006.01)
G16H 50/30 (2018.01)
G16H 20/60 (2018.01)

(52) U.S. Cl.
CPC .......... *A61B 5/7275* (2013.01); *A61B 5/0002* (2013.01); *A61B 5/486* (2013.01); *A61B 5/4875* (2013.01); *A61B 5/743* (2013.01); *G01G 19/44* (2013.01); *G09B 19/00* (2013.01); *G16H 20/60* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 6,516,221 B1* | 2/2003 | Hirouchi | A61B 5/0537 600/547 |
| 2002/0022773 A1* | 2/2002 | Drinan | A61B 5/0537 600/300 |
| 2002/0112898 A1* | 8/2002 | Honda | A61B 5/4869 177/245 |
| 2003/0046009 A1* | 3/2003 | Honda | G01G 19/50 702/19 |
| 2006/0015016 A1* | 1/2006 | Thornton | G06Q 10/00 600/300 |

(Continued)

OTHER PUBLICATIONS

Renato Romani, "WOA APP"; Dec. 14, 2013; https://www.youtube.com/watch?v=bHoZ89Glc9g&list=PLPE0IT_CAY_qzBYpGfoSqs5ZtbhQoiDpP&index=5 (Year: 2013).*

(Continued)

*Primary Examiner* — James B Hull
(74) *Attorney, Agent, or Firm* — Joseph T. Miotke; Erin Ella Block; DeWitt LLP

(57) ABSTRACT

A system and method for determining the weight gain trend of a user. The weekly weight oscillation is determined, and a future weight trend can be predicted. At least three weeks of weight oscillation trends are typically used to predict future weight trends.

18 Claims, 11 Drawing Sheets

(56) References Cited

U.S. PATENT DOCUMENTS

| | | | |
|---|---|---|---|
| 2008/0004501 A1* | 1/2008 | Gavrilov | G01G 19/4146 600/300 |
| 2009/0234916 A1* | 9/2009 | Cosentino | G01G 23/3742 709/203 |
| 2010/0130831 A1* | 5/2010 | Sato | G01G 23/3728 600/300 |
| 2010/0227302 A1* | 9/2010 | McGilvery | A61B 5/4866 434/236 |
| 2011/0106553 A1* | 5/2011 | Sato | A61B 5/4869 705/2 |
| 2012/0244995 A1* | 9/2012 | Dibenedetto | A61B 5/0024 482/9 |
| 2013/0054271 A1* | 2/2013 | Langford | G06Q 50/24 705/3 |
| 2013/0091454 A1* | 4/2013 | Papa | G16H 20/60 715/772 |
| 2013/0198214 A1* | 8/2013 | Hall | G06F 19/3481 707/758 |
| 2013/0252211 A1* | 9/2013 | Oshima | A61B 5/0537 434/127 |
| 2013/0317386 A1* | 11/2013 | Sumino | A61B 5/7275 600/547 |
| 2014/0090444 A1* | 4/2014 | Onomatsu | G01G 19/44 73/1.13 |
| 2014/0155760 A1* | 6/2014 | Ridder | A61B 5/1171 600/479 |
| 2014/0212850 A1* | 7/2014 | Shimizu | A61B 5/0537 434/127 |
| 2014/0224552 A1* | 8/2014 | Shimizu | G06F 19/3475 177/25.13 |
| 2014/0343443 A1* | 11/2014 | Yuen | G01G 23/3728 600/509 |
| 2014/0344192 A1* | 11/2014 | Akai | G16H 20/60 706/11 |
| 2015/0093725 A1* | 4/2015 | Baarman | G09B 5/02 434/127 |
| 2015/0130830 A1* | 5/2015 | Nagasaki | G06Q 10/0639 345/592 |
| 2015/0161911 A1* | 6/2015 | Muto | G06F 19/3475 434/127 |
| 2015/0324540 A1* | 11/2015 | Moloney-Egnatios | G06F 19/322 705/3 |
| 2015/0339949 A1* | 11/2015 | Landers | G16H 40/63 434/127 |
| 2017/0084195 A1* | 3/2017 | Roberts | G16H 20/60 |
| 2017/0176239 A1* | 6/2017 | Pan | G01G 19/44 |
| 2017/0340269 A1* | 11/2017 | McGilvery | A61B 5/4866 |
| 2018/0003547 A1* | 1/2018 | Ten Kate | A43B 3/0005 |
| 2018/0052957 A1* | 2/2018 | Finkelmeier | A61B 5/04012 |
| 2018/0224323 A1* | 8/2018 | Hashizume | G01G 19/4146 |
| 2018/0228432 A1* | 8/2018 | Woo | A61B 5/0537 |
| 2018/0294053 A1* | 10/2018 | Runyon | G06N 7/00 |
| 2019/0255239 A1* | 8/2019 | Goto | A61M 1/1601 |
| 2020/0077952 A1* | 3/2020 | Baek | A61B 5/486 |

OTHER PUBLICATIONS

Renato Romani, "WOA description and graphs"; Oct. 24, 2013; https://www.youtube.com/watch?v=n9Ja2sWQPFA&list=PLPE0IT_CAY_qzBYpGfoSqs5ZtbhQoiDpP&index=7 (Year: 2013).*
Renato Romani, "WOA Scale & Interface"; Oct. 25, 2013; https://www.youtube.com/watch?v=ylefh70ixJ0&list=PLPE0IT_CAY_qzBYpGfoSqs5ZtbhQoiDpP&index=6 (Year: 2013).*
Renato Romani, "WOA Algorithm movie"; Jun. 21, 2013; https://www.youtube.com/watch?v=Qrn8mbSFuu0 (Year: 2013).*
Renato Romani; "WIFI scale explan"; Jul. 26, 2013; https://www.youtube.com/watch?v=4gmP4ixBoKs&list=UURcu8tM3-9mD_8RhqpMxKUQ&index=88 (Year: 2013).*
International Preliminary Report on Patentability for PCT/US16/66624 dated Jun. 28, 2018.
International Search Report for PCT/US16/66624 dated Mar. 10, 2017.
Aoi Barnes J. "A randomised, controlled trial with internal pilot of a weight loss maintenance intervention for obese adults after clinically significant weight loss", [Internet]. http: //isrctn.org/>. ISRCTN, London, UK; 2014 [cited Mar. 20, 2014]. Available from: http://www.isrctn.com/ISRCTN14657176.
Aoi W, Ueda Y, Tanigawa M. "Effect of weight loss on the reduction of blood pressure in obesity hypertension-hyperinsulinemia and renal sodium retention", 1992. Nihon Jinzo Gakkai shi [Internet]. 34:1177-82. Available from: http://www.ncbi.nlm.nih.gov/pubmed/1294771.
Benn Y, Webb TL, Chang BPI, Harkin B. "What is the psychological impact of self-weighing? A meta-analysis.", Health Psychology Review [Internet]. Apr. 2, 2016 [cited Apr. 2, 2016]; 10:187-203. Available from: http://www.tandfonline.com/doi/abs/10.1080/17437199.2016.1138871.
Benton David, Kimberly T Jenkins, Heather T Watkins, Hayley A Young, "Minor degree of hypohydration adversely influences cognition: a mediator analysis", [Internet]. Am J Clin Nutr. Sep. 2016;104(3):603-12. Available from: https://www.ncbi.nlm.nih.gov/pubmed/27510536.
Burke LE, Wang J, Sevick MA. "Self-monitoring in weight loss: a systematic review of the literature". Journal of the American Dietetic Association [Internet]. Jan. 1, 2011 [cited Jan. 1, 2011];111:92-102. Available from: http://www.ncbi.nlm.nih.gov/pubmed/21185970.
Calugi S, Marchesini G, El Ghoch M, Gavasso I, Dalle Grave R. "The Influence of Weight-Loss Expectations on Weight Loss and of Weight-Loss Satisfaction on Weight Maintenance in Severe Obesity". Journal of the Academy of Nutrition and Dietetics [Internet]. Oct. 22, 2016. Available from http://www.ncbi.nlm.nih.gov/pubmed/27780692.
Chang BPI, Webb TL, Benn Y. "Why Do People Act Like the Proverbial Ostrich? Investigating the Reasons That People Provide for Not Monitoring Their Goal Progress". Frontiers in Psychology [Internet]. Feb. 8, 2017 [cited Feb. 8, 2017];8. Available from: http://journal.frontiersin.org/article/10.3389/fpsyg.2017.00152/full.
Coles LT, Fletcher EA, Galbraith CE, Clifton PM. "Patient freedom to choose a weight loss diet in the treatment of overweight and obesity: a randomized dietary intervention in type 2 diabetes and pre-diabetes". The international journal of behavioral nutrition and physical activity [Internet]. May 16, 2014 [cited May 16, 2014];11:64. Available from: http://www.ncbi.nlm.nih.gov/pubmed/24886191.
Crawford R, Glover L. "The impact of pre-treatment weight-loss expectations on weight loss, weight regain, and attrition in people who are overweight and obese: a systematic review of the literature". British journal of health psychology [Internet]. 2012. 17:609-30. Available from: http://www.ncbi.nlm.nih.gov/pubmed/22151728.
Cunningham E. "What impact does water consumption have on weight loss or weight loss maintenance?" Journal of the Academy of Nutrition and Dietetics [Internet]. 2014, 114:2084. Available from: http://www.ncbi.nlm.nih.gov/pubmed/25458752.
Daley Amanda J., K. Jolly, S. A. Jebb, A. K. Roalfe, L. Mackillop, A. L. Lewis, S. Clifford, S. Kenyon, C. MacArthur and P. Aveyard. "Effectiveness of regular weighing, weight target setting and feedback by community midwives within routine antenatal care in preventing excessive gestational weight gain: randomised controlled trial", (2016) 3:7, BMC Obesity. Available at:https://bmcobes.biomedcentral.com/articles/10.1186/s40608-016-0086-4.
Daley A, Jolly K, Madigan C, Griffin R, Roalfe A, Lewis A, Nickless A, Aveyard P. "A brief behavioural intervention to promote regular self-weighing to prevent weight regain after weight loss: a RCT". Southampton (UK): NIHR Journals Library; Apr. 2019. PMID: 31042335 Free Books & Documents. Review. Available at:https://www.researchgate.net/publication/332808030_A_brief_behavioural_intervention_to_promote_regular_selfweighing_to_prevent_weight_regain_after_weight_loss_a_RCT.
Delahanty LM, Pan Q, Jablonski KA, Aroda VR, Watson KE, Bray GA, et al., "Diabetes Prevention Program Research Group. Effects of weight loss, weight cycling, and weight loss maintenance on diabetes incidence and change in cardiometabolic traits in the

(56) References Cited

OTHER PUBLICATIONS

Diabetes Prevention Program.", 2014. Diabetes care [Internet]. 37:2738-45. Available from: http://www.ncbi.nlm.nih.gov/pubmed/25024396.

Fogari Roberto, Annalisa Zoppi, Luca Corradi, Paola Preti, Amedeo Mugellini, Pierangelo Lazzari, Giuseppe Derosa, "Effect of body weight loss and normalization on blood pressure in overweight non-obese patients with stage 1 hypertension", 2010. Available at:https://pubmed.ncbi.nlm.nih.gov/20075930/.

Gage D. "Weight loss/maintenance as an effective tool for controlling type 2 diabetes: novel methodology to sustain weight reduction", 2012. Diabetes/metabolism research and reviews [Internet]. 28:214-8. Available from: http://www.ncbi.nlm.nih.gov/pubmed/22215481.

Haüssinger D., Gerok W., Roth E.,Lang F.,"Cellular hydration state: an important determinant of protein catabolism in health and disease". Published: May 22, 1993. The LANCET Regional Health. Available at: http://www.thelancet.com/journals/lancet/article/PII0140-6736(93)90828-5/abstract.

Jones Leon C, Michelle A Cleary, Rebecca M Lopez, Ron E Zuri, Richard Lopez. "Active dehydration impairs upper and lower body anaerobic muscular power", J Strength Cond Res, National Library of Medicine, National Center for Biotechnology Information, Mar. 2008;22(2):455-63. Available at: https://www.ncbi.nlm.nih.gov/pubmed/18550960.

Kraft Justin A., James M Green, Phillip A Bishop, Mark T Richardson, Yasmin H Neggers, James D Leeper, "The influence of hydration on anaerobic performance: a review". National Library of Medicine, National Center for Biotechnology Information,Jun. 2012;83(2):282-92, Available at:https://www.ncbi.nlm.nih.gov/pubmed/22808714.

Kuller LH. "Weight loss and reduction of blood pressure and hypertension. Hypertension" (Dallas, Tex: 1979) [Internet] 2020, 54:700-1. Available from: http://www.ncbi.nlm.nih.gov/pubmed/19704102.

LaRose JG, Fava JL, Steeves EA, Hecht J, Wing RR, Raynor HA. "Daily self-weighing within a lifestyle intervention: impact on disordered eating symptoms." Health psychology: official journal of the Division of Health Psychology, American Psychological Association [Internet]. Mar. 18, 2014 [cited Mar. 18, 2014];33:297-300. Available from: http://www.ncbi.nlm.nih.gov/pubmed/24245845.

LaRose JG, Lanoye A, Tate DF, Wing RR. "Frequency of self-weighing and weight loss outcomes within a brief lifestyle intervention targeting emerging adults: Self-weighing in emerging adults". Obesity Science & Practice [Internet]. Mar. 1, 2016 [cited Mar. 1, 2016];2. Available from: http://doi.wiley.com/10.1002/osp4.24.

Leermakers EA, Perri MG, Shigaki CL, Fuller PR. "Effects of exercise-focused versus weight-focused maintenance programs on the management of obesity". Addict Behav [Internet]. 1997 [cited 1997];24:219-27. Available from: http://www.ncbi.nlm.nih.gov/pubmed/10336103.

Linde JA, Jeffery RW, French SA, Pronk NP, Boyle RG. "Self-weighing in weight gain prevention and weight loss trials" 2005. Annals of behavioral medicine: a publication of the Society of Behavioral Medicine [Internet]. 30:210-6. Available from: http://www.ncbi.nlm.nih.gov/pubmed/16336072.

Madigan CD, Aveyard P, Jolly K, Denley J, Lewis A, Daley AJ. "Regular self-weighing to promote weight maintenance after intentional weight loss: a quasi-randomized controlled trial". Jun. 2013. Journal of public health (Oxford, England) [Internet]. 36:259-67. Available from: http://www.ncbi.nlm.nih.gov/pubmed/23753256.

Madigan CD, Jolly K, Lewis AL, Aveyard P, Daley AJ. "A randomised controlled trial of the effectiveness of self-weighing as a weight loss intervention". The international journal of behavioral nutrition and physical activity [Internet]. Oct. 10, 2014 [cited Oct. 10, 2014];11:125. Available from: http://www.ncbi.nlm.nih.gov/pubmed/25301251.

Madigan CD, Jolly K, Roalfe A, Lewis AL, Webber L, Aveyard P, et al. "Study protocol: the effectiveness and cost effectiveness of a brief behavioural intervention to promote regular self-weighing to prevent weight regain after weight loss": randomised controlled trial (The LIMIT Study). BMC public health [Internet]. Jun. 4, 2015 [cited Jun. 4, 2015];15:530. Available from: http://www.ncbi.nlm.nih.gov/pubmed/26041653.

Madigan CD, Daley AJ, Lewis AL, Aveyard P, Jolly K. "Is self-weighing an effective tool for weight loss: a systematic literature review and meta-analysis". Aug. 21, 2015. The international journal of behavioral nutrition and physical activity [Internet]. 12:104. Available from: http://www.ncbi.nlm.nih.gov/pubmed/26293454.

Mainous AG, Diaz VA, Koopman RJ, Everett CJ. "Having a regular physician and attempted weight loss after screening for hypertension or hypercholesterolemia", 2005. International journal of obesity (2005) [Internet]. 29:223-7. Available from: http://www.ncbi.nlm.nih.gov/pubmed/15558075.

McCarthy WJ, Arpawong TE, Dietsch BJ, Yancey AK. "Effects of exercise and weight loss on hypertension", 2003. JAMA [Internet]. 290:885; author reply 886-885; author reply 887. Available from: http://www.ncbi.nlm.nih.gov/pubmed/12928458.

Mengham L, Morris B, Palmer C, White A. "Is intensive dietetic intervention effective for overweight patients with diabetes mellitus? A randomized controlled study in a general practice", 1999. Practical Diabetes International [Internet]. 16. Available from: http://doi.wiley.com/10.1002/pdi.1960160107.

Metzgar CJ, Preston AG, Miller DL, Nickols-Richardson SM. "Facilitators and Barriers to Weight Loss and Weight Loss Maintenance" Questionnaire [Internet]. PsycTESTS Dataset. APA; 2016 [cited Jul. 11, 2016]. Available from: http://doi.apa.org/getdoi.cfm?doi=10.1037/t51373-000.

Norris SL, Zhang X, Avenell A, Gregg E, Bowman B, Schmid CH, et al. "Long-term effectiveness of weight-loss interventions in adults with pre-diabetes: a review", 2005. American journal of preventive medicine [Internet]. 28:126-39. Available from: http://www.ncbi.nlm.nih.gov/pubmed/15626569.

Oshima Y, Matsuoka Y, Sakane N. "Effect of weight-loss program using self-weighing twice a day and feedback in overweight and obese subject: a randomized controlled trial", 2013, Obesity research & clinical practice [Internet]. 7:e361-6. Available from: http://www.ncbi.nlm.nih.gov/pubmed/24304478.

Pacanowski CR, Levitsky DA. "Frequent Self-Weighing and Visual Feedback for Weight Loss in Overweight Adults", 2015. Journal of obesity [Internet]. 2015:763680. Available from: http://www.ncbi.nlm.nih.gov/pubmed/26064677.

Catarina Paixão Carlos M. Dias Rui Jorge Eliana V. Carraça Mary Yannakoulia Martina de Zwaan Sirpa Soini James O. Hill Pedro J. Teixeira Inês Santos, "Successful weight loss maintenance: A systematic review of weight control registries", First published: Feb. 12, 2020 Available at: https://doi.org/10.1111/obr.13003Citations: 10.

Pirkola J, Pouta A, Bloigu A, Hartikainen A-L, Laitinen J, Järvelin M-R, et al. "Risks of overweight and abdominal obesity at age 16 years associated with prenatal exposures to maternal prepregnancy overweight and gestational diabetes mellitus". 2010. Diabetes care [Internet]. 33:1115-21. Available from: http://www.ncbi.nlm.nih.gov/pubmed/20427685.

Barry M. Popkin, Kristen E. D'Anci, and Irwin H. Rosenberg, "Water, Hydration and Health", National Institute of Health, 2010. Available at: https://www.ncbi.nlm.nih.gov/pmc/articles/PMC2908954/.

Raynor HA, Jeffery RW, Ruggiero AM, Clark JM, Delahanty LM, "Weight loss strategies associated with BMI in overweight adults with type 2 diabetes at entry into the Look AHEAD (Action for Health in Diabetes) trial".2008, Diabetes care [Internet]. 31:1299-304. Available from: http://www.ncbi.nlm.nih.gov/pubmed/18375417.

Resnick L. "Effect of modest weight loss on arterial compliance in essential hypertension". 2001. American Journal of Hypertension [Internet]. Available from: https://academic.oup.com/ajh/article-lookup/doi/10.1016/S0895-7061(01)01457-1.

Ritz, P.et al, "Effects of changes in water compartments on physiology and metabolism", Dec. 18, 2003. Available at: https://www.nature.com/articles/1601894.

Robertson S, Davies M, Winefield H. "Positive psychological correlates of successful weight maintenance in Australia: Weight

(56) References Cited

OTHER PUBLICATIONS loss maintenance". Clinical Psychologist [Internet]. 2015. Available from: http://doi.wiley.com/10.1111/cp.12073.
Sarrafan-Chaharsoughi Z. "The High Prevalence of Overweight and Obesity in Patients with Diabetes Mellitus in Yazd". J ournal of Diabetes and Obesity [Internet]. 2013 [cited 2013];2. Available from: http://www.ommegaonline.org/article-details/The-High-Prevalence-of-Overweight-and-Obesity-in-Patients-with-Diabetes-Mellitus-in-Yazd/413.
Sauchelli Sarah, Julia Bradley, Jennifer Cox, Clare England and Rachel Perry, "Weight maintenance interventions for people with type 2 diabetes mellitus: a systematic review protocol". BMC, Systematic Reviews, Available at https://doi.org/10.1186/s13643-020-01467-7.
Schreiner B. "Promoting Lifestyle and Behavior Change in Overweight Children and Adolescents With Type 2 Diabetes". Diabetes Spectrum [Internet]. Jan. 1, 2005 [cited Jan. 1, 2005];18. Available from: http://spectrum.diabetesjournals.org/cgi/doi/10.2337/diaspect.18.1.9.
Shieh, C., Knisely, M. R., Clark, D., & Carpenter, J. S. (2016). "Self-weighing in weight management interventions: A systematic review of literature". Obesity Research & Clinical Practice. http://doi.org/10.1016/j.orcp.2016.01.004.
Sniehotta Falco R. et al., "Behavioural intervention for weight loss maintenance versus standard weight advice in adults with obesity: A randomised controlled trial in the UK (NULevel Trial)", 2019, Available at: https://doi.org/10.1371/journal.pmed.1002793.
Soleymani T, Daniel S, Garvey WT. "Weight maintenance: challenges, tools and strategies for primary care physicians", 2015. Obesity reviews: an official journal of the International Association for the Study of Obesity [Internet]. 17:81-93. Available from: http://www.ncbi.nlm.nih.gov/pubmed/26490059.
Steinberg DM, Tate DF, Bennett GG, Ennett S, Samuel-Hodge C, Ward DS. "The efficacy of a daily self-weighing weight loss intervention using smart scales and e-mail". Obesity (Silver Spring, Md) [Internet]. Sep. 2, 2013 [cited Sep. 2, 2013];21:1789-97. Available from: http://www.ncbi.nlm.nih.gov/pubmed/23512320.
Steinberg DM, Bennett GG, Askew S, Tate DF. "Weighing every day matters: daily weighing improves weight loss and adoption of weight control behaviors", 2016. Journal of the Academy of Nutrition and Dietetics [Internet]. 115:511-8. Available from: http://www.ncbi.nlm.nih.gov/pubmed/25683820.
Stookey JD, Constant F, Popkin BM, Gardner CD, "Drinking water is associated with weight loss in overweight dieting women independent of diet and activity". Sports Nutrition: Olympic Handbook of Sports Medicine Ronald Maughan 2008. Available at: https://www.ncbi.nlm.nih.gov/pubmed/18787524raynor.
Ericson John, "10. 75% of Americans May Suffer From Chronic Dehydration, According to Doctors" Jul. 3, 2013. Available at: http://www.medicaldaily.com/75-americans-may-suffer-chronic-dehydration-according-doctors-247393.
Stroebele N, de Castro JM, Stuht J, Catenacci V, Wyatt HR, Hill JO. "A Small-Changes Approach Reduces Energy Intake in Free-Living Humans". Journal of the American College of Nutrition [Internet]. Feb. 1, 2009 [cited Feb. 1, 2009];28:63-8. Available from: http://www.tandfonline.com/doi/abs/10.1080/07315724.2009.10719763.
Tayek JA. "Is weight loss a cure for type 2 diabetes?", 2002, Diabetes care [Internet]. 25:397-8. Available from: http://www.ncbi.nlm.nih.gov/pubmed/11815518.
Teixeira PJ, Silva MN, Mata J, Palmeira AL, Markland D. "Motivation, self-determination, and long-term weight control". The international journal of behavioral nutrition and physical activity [Internet]. Mar. 2, 2012 [cited Mar. 2, 2012];9:22. Available from: http://www.ncbi.nlm.nih.gov/pubmed/22385818.
Thorndike Anne, MD, MPH. Lillian Sonnenberg, DSc, RD. Erica Healey, MA. Khinlei Myint-U, MBA. Joseph C. Kvedar, MD. Susan Regan, PhD, "Prevention of Weight Gain Following a Worksite Nutrition and Exercise Program. A Randomized Controlled Trial", 2012. Available at: https://www.ncbi.nlm.nih.gov/pmc/articles/PMC3377937/.
University of Utah, "Is Eight Enough? U Researcher Says Drink Up and Tells Why", 2003, Available from: https://healthcare.utah.edu/publicaffairs/news/archive/2003/news_74.php.
VanWormer JJ, Martinez AM, Martinson BC, Crain AL, Benson GA, Cosentino DL, et al. Self-weighing promotes weight loss for obese adults, 2003. American journal of preventive medicine [Internet]. 36:70-3. Available from: http://www.ncbi.nlm.nih.gov/pubmed/18976879.
VanWormer JJ, Linde JA, Harnack LJ, Stovitz SD, Jeffery RW. "Self-weighing frequency is associated with weight gain prevention over 2 years among working adults", 2012. International journal of behavioral medicine [Internet]. 19:351-8. Available from: http://www.ncbi.nlm.nih.gov/pubmed/21732212.
Welsh Ericka M., Nancy E Sherwood, Jeffrey J VanWormer, Anne Marie Hotop, Robert W Jeffery. "Is frequent self-weighing associated with poorer body satisfaction? Findings from a phone-based weight loss trial", 2009. Available at: https://pubmed.ncbi.nlm.nih.gov/19879499/.
West DS, Gorin AA, Subak LL, Foster G, Bragg C, Hecht J, et al., "A motivation-focused weight loss maintenance program is an effective alternative to a skill-based approach". Program to Reduce Incontinence by Diet and Exercise (PRIDE) Research Group. 2011, International journal of obesity [Internet]. 35:259-69. Available from: http://www.ncbi.nlm.nih.gov/pubmed/20680012.
Wing RR, Venditti E, Jakicic JM, Polley BA, Lang W. "Lifestyle intervention in overweight individuals with a family history of diabetes". 1998, Diabetes care [Internet]. 21:350-9. Available from: http://www.ncbi.nlm.nih.gov/pubmed/9540015.
Zheng Y, Klem ML, Sereika SM, Danford CA, Ewing LJ, Burke LE. "Self-weighing in weight management: a systematic literature review". Obesity (Silver Spring, Md) [Internet]. Feb. 17, 2015 [cited Feb. 17, 2015];23:256-65. Available from: http://www.ncbi.nlm.nih.gov/pubmed/25521523.

\* cited by examiner

WEIGHT MANAGEMENT SYSTEM

CROSS-REFERENCES TO RELATED APPLICATIONS

This application is the U.S. national stage application of International Application No. PCT/US2016/066624, filed Dec. 14, 2016, which international application was published on Jun. 22, 2017 as International Publication No. WO2017/106320. The International Application claims the benefit d prior-filed, U.S. Provisional Patent Application No. 62/267,459, filed Dec. 15, 2015, the entire contents of which are incorporated herein by reference.

BACKGROUND OF THE INVENTION

Obesity is linked to higher risks of developing chronic medical conditions (such as diabetes and heart disease) and diminished quality of life. The problem has only been getting worse, with the rate of obesity in both adults and children dramatically higher now than it was 20 years ago. The toll obesity takes on the population is not only in increased morbidity and mortality, but higher healthcare costs and increased absenteeism from work and school.

Compounding the problem are the difficulties faced when trying to lose weight. It usually requires a significant change in habits (diet and activity level) over an extended period of time. Even when a person does the right things, his or her weight does not generally decrease in a uniform or consistent manner. Rather, a person's weight tends to fluctuate on a weekly or even daily basis. Moreover, soon after a person lowers caloric intake or increases calories burned, his or her body usually reacts by attempting to increase fat reserves at a "new normal" by (for example) making adjustments to the person's metabolism. This often leads to a decrease in the rate of weight loss or a plateau, which can demotivate a person struggling to lose weight. If a person whose weight loss has plateaued does not have useful information on how his or her efforts are expected to result in continued weight loss over time, the person may become demoralized, cease weight loss efforts, and potentially pick up (or return to) an unhealthy lifestyle.

There exists a continuing need for a system for monitoring weight over time in order to provide useful information about weight trends and anticipated weight change. Preferably such a system is not imposing or inconvenient so that users are more likely to continue monitoring their progress and stick with their weight loss efforts.

BRIEF SUMMARY OF THE INVENTION

While weight is typically the most simple medical parameter to measure, the number at the scale represents the total body weight at that moment. At different moments of a day, a person's body will typically have a different weight. The typical reason for such weight fluctuation throughout the day is the body's use and loss of water. The typical weight fluctuation associated with water gain and loss can be three or more pounds per day. Accordingly, one of the primary factors affecting daily weight fluctuation typically related to how the body uses water, which is also related to the gain or other consumption of elements that comprise human tissues and cells.

Exemplary versions of the present invention typically use a person's weight to generate predictions about future weight. The system typically collects at least three weight readings in a week, taken on different days of the week (i.e., readings from at least three days). Because short-term oscillations in weight can mask overall trends in weight change, the system typically obtains data for three weeks before providing the user with information on weight trend. Once the system has three weeks of data, the user typically can be provided with predictions about future weight at subsequent measurements. The trend could be that the user is gaining weight, maintaining weight, or losing weight. Because this system requires minimal information (i.e., only weight), it is typically much more convenient (and thus more likely to be successfully used) than other systems that additionally collects (for example) data on body fat, blood pressure, body temperature, blood test results, diet, activity, etc. The system of the present application typically improves on (and gives more meaning to) the measurements of weight scales by uncovering the real weight trends that are hidden by daily weight oscillations.

The system of the present invention typically uses an algorithm that can clean the noise created by water weight fluctuation when making weight trend predictions. FIGS. 1 and 2 illustrate the typically confusing, and sometimes incorrect, weight trend conclusions that can be drawn from the same overall weight fluctuation depending upon the moments at which the weight measurements are taken. The overall weight fluctuation graph 100 is the same in both FIGS. 1 and 2. Referring to FIG. 1, a user might have the impression that the user is losing weight based upon the downward sloping line 120 resulting when weight measurements are taken at moments 122, 124, 126, and 128. Referring to FIG. 2, the same user might likewise have the impression that the user is gaining weight based upon the upward sloping line resulting when weight measurements are taken at moments 132, 134, 136, and 138. In one aspect, the system of the present application can learn the weight oscillation as shown in graph 100, clean the noise from this oscillation and then determine and predict the momentum of the user weight gain.

A user may begin by having his or her weight measured using a scale located at (for example) work, home, school, or a clinic. This could occur shortly after the user has been identified, or it could occur beforehand. The user may be asked to enter information about what clothing he or she is wearing so that adjustments can be made to account for the weight of the user's clothing. Weight readings can be stored and/or processed locally, automatically transmitted (via wireless or wired means) to another computing device for remote storage and/or processing, and/or physically transferred to another device (such as by moving a suitable storage medium with the data). The readings (and oscillations therein) are analyzed to extract information on trends. The analysis uses data on the time between two readings, the change in weight, and the rate of change in weight. By taking multiple readings over different days, outliers can be accounted for (such as a weight measurement taken when a person is dehydrated following an exercise session). Generally, the more weight readings are available for a user, the better the trend information.

Once enough past weight measurements are available, the user is provided with a prediction regarding future weight. For example, the user may be provided (via a computing device with a display) a bar chart showing weight variation in the past three weeks, and a prediction about weight in the coming two weeks. The prediction could be an expected weight with margin of error information, or it could visually depict the expected weight range with a particular level of certainty (such as 95% or 99%). Measured weights of users over time could be aggregated (on an anonymous basis) for data mining and to enhance future weight prediction.

The manner of collecting users' weight (information input) can be tailored for different settings and applications. For example, weight can be obtained via manual input at a terminal or an Internet website. Or, a weight scale able to transmit data (via, for example, Wi-Fi or Bluetooth) can be instructed to transmit readings to another system (directly or via an intermediary). Or, a specialized weight scale tasked with collecting weight information can be used. These devices can be owned and/or operated by a single entity, or different devices in the overall system can be operated by affiliated or unaffiliated third parties. The manner of providing users with results (information output) can be via any communication and/or display device. For example, a user can receive information via a stand-alone interface, kiosk, or scale that is operated by the same entity that processes user weight information, or via personal mobile devices such as smartphones and tablets, or via any computing device able to access a server via a network. Information need not only be provided visually but can also be provided via (for example) words spoken by a computing device.

DETAILED DESCRIPTION OF THE INVENTION

1. System Overview

Figure 1:
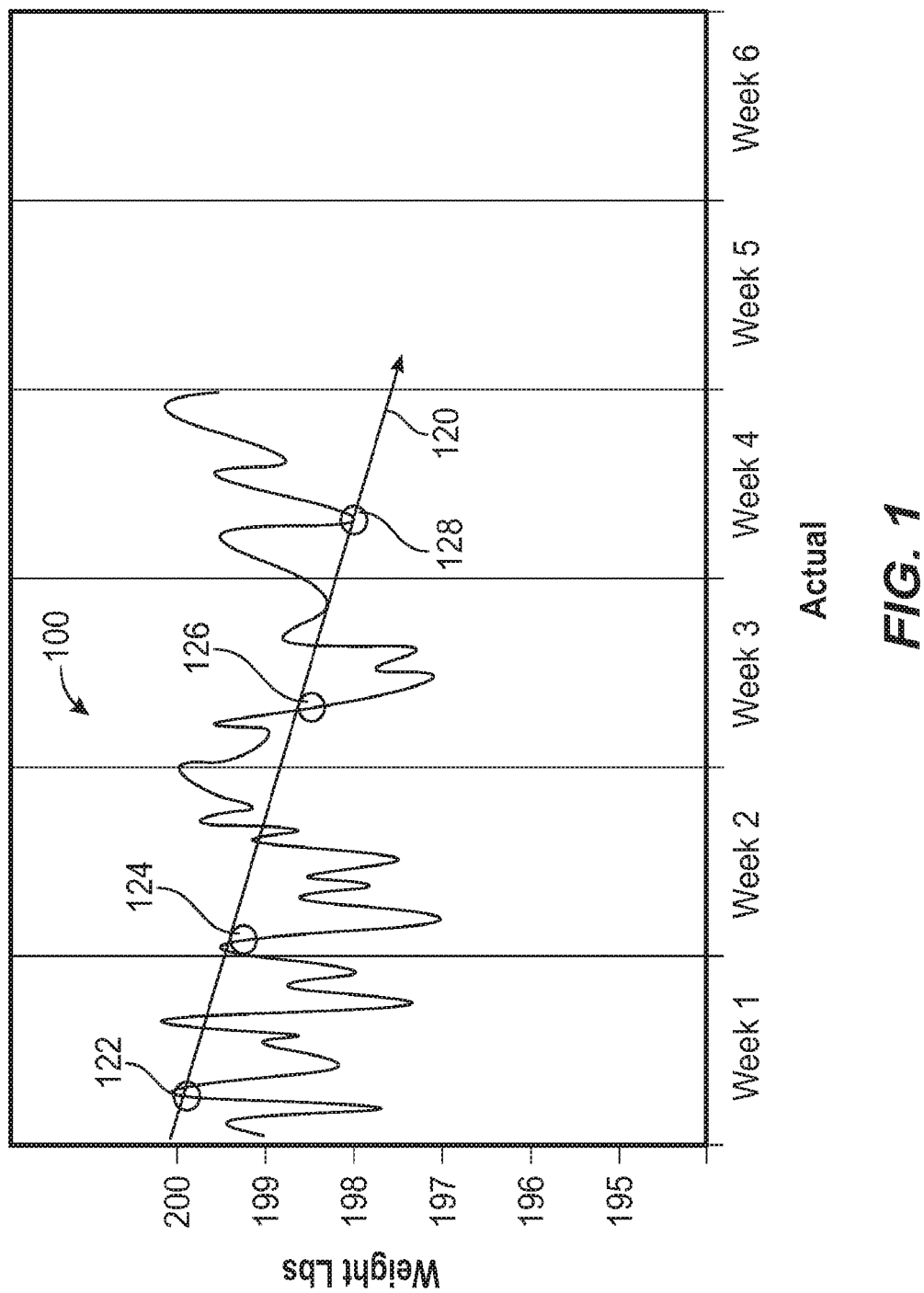
FIG. 1 provides a weight trend graph according to one aspect of the application.
Figure 2:
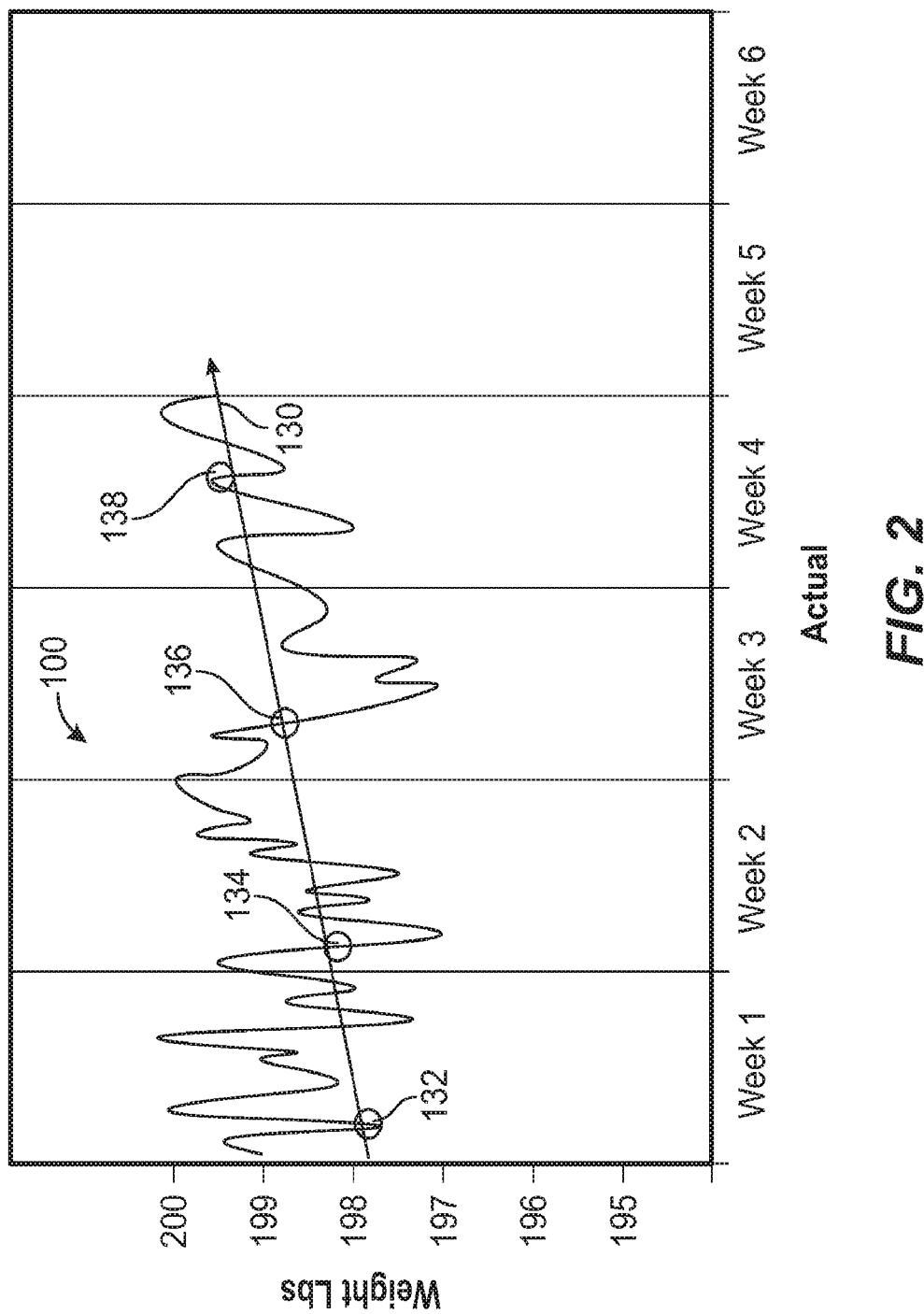
FIG. 2 provides another weight trend graph according to one aspect of the application.
Figure 3:
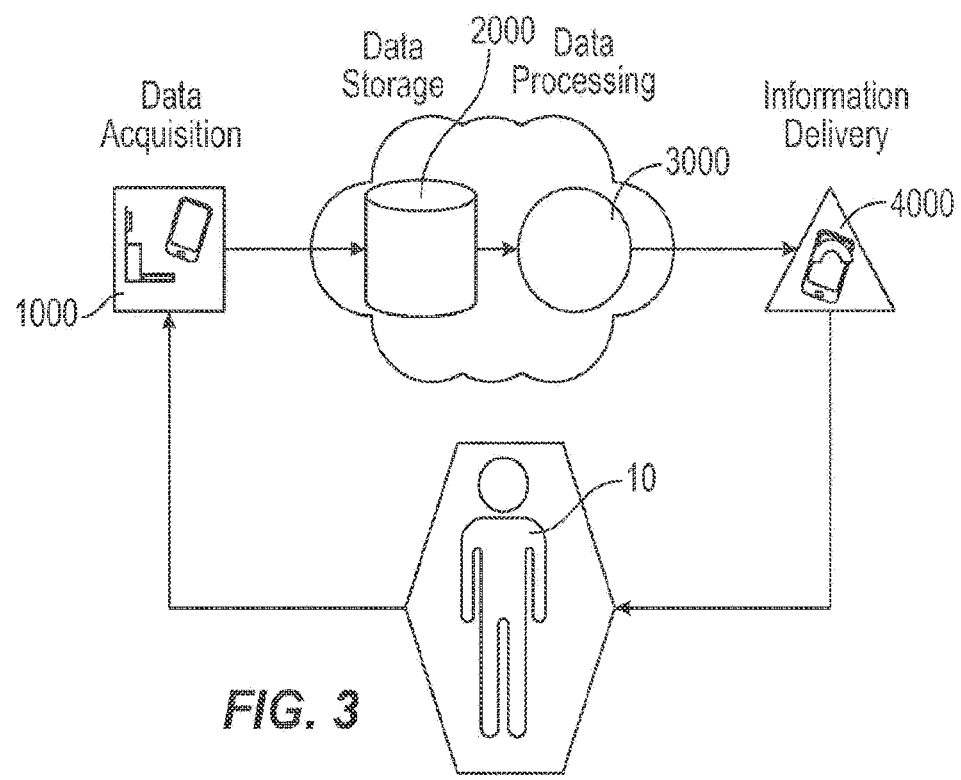
FIG. 3 provides an illustrative overall system view according to one aspect of the application.

Referring to FIG. 3, an overall view of a nonlimiting, exemplary depiction of the typical components of the system according to an aspect of the present application is shown. A data acquisition subsystem 1000 typically collects input from a user 10. Subsystem 1000 typically transmits data and other information to data storage subsystem 2000. Subsystem 2000 typically communicates with data processing subsystem 3000, and subsystem 3000 typically performs a variety of calculations, analytics, and other analyses upon the data. Subsystem 3000 communicates with information delivery subsystem 4000, and subsystem 4000 typically delivers information to user 10. It will be understood that while the foregoing systems are described as separate systems, it is to be recognized that implementations of such systems can be performed using one or more processors, which may be communicatively connected, and such implementations are considered to be within the scope of the description. In addition, such subsystems could be combined into one another without departing from the scope of the present application. Furthermore, the foregoing subsystems can communicate using any available communication methodologies, including both wired and wireless communications, and combinations thereof.

2. Weight/Data Acquisition

Figure 4:
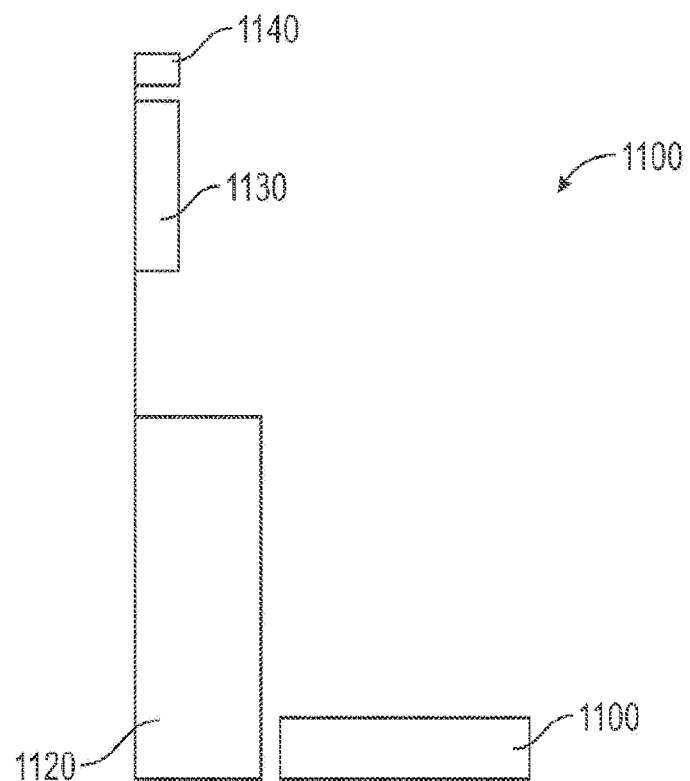
FIG. 4 provides an illustrative component diagram of an illustrative weight tracking station according to one aspect of the application.

Referring now to FIG. 4, a weight tracking station 1100 according to one aspect of the present application is shown. Station 1100 provides one example of data acquisition subsystem 1000 according to an aspect of the present application. Station 1100 typically can include a scale 1110, computer processing unit 1120, touch screen monitor 1130, and camera 1140. Scale 1100 measures the weight of a user (not shown) and transmits the measured weight to processing unit 1120. In one aspect, scale 1110 communicates wirelessly with unit 1120 (e.g., using Wi-Fi or Bluetooth). In other aspects, scale 1110 can be interfaced with unit 1120 using other implementations such as wired connections. Unit 1120 is in communication with touch screen monitor 1130 and camera 1140.

Figure 5:
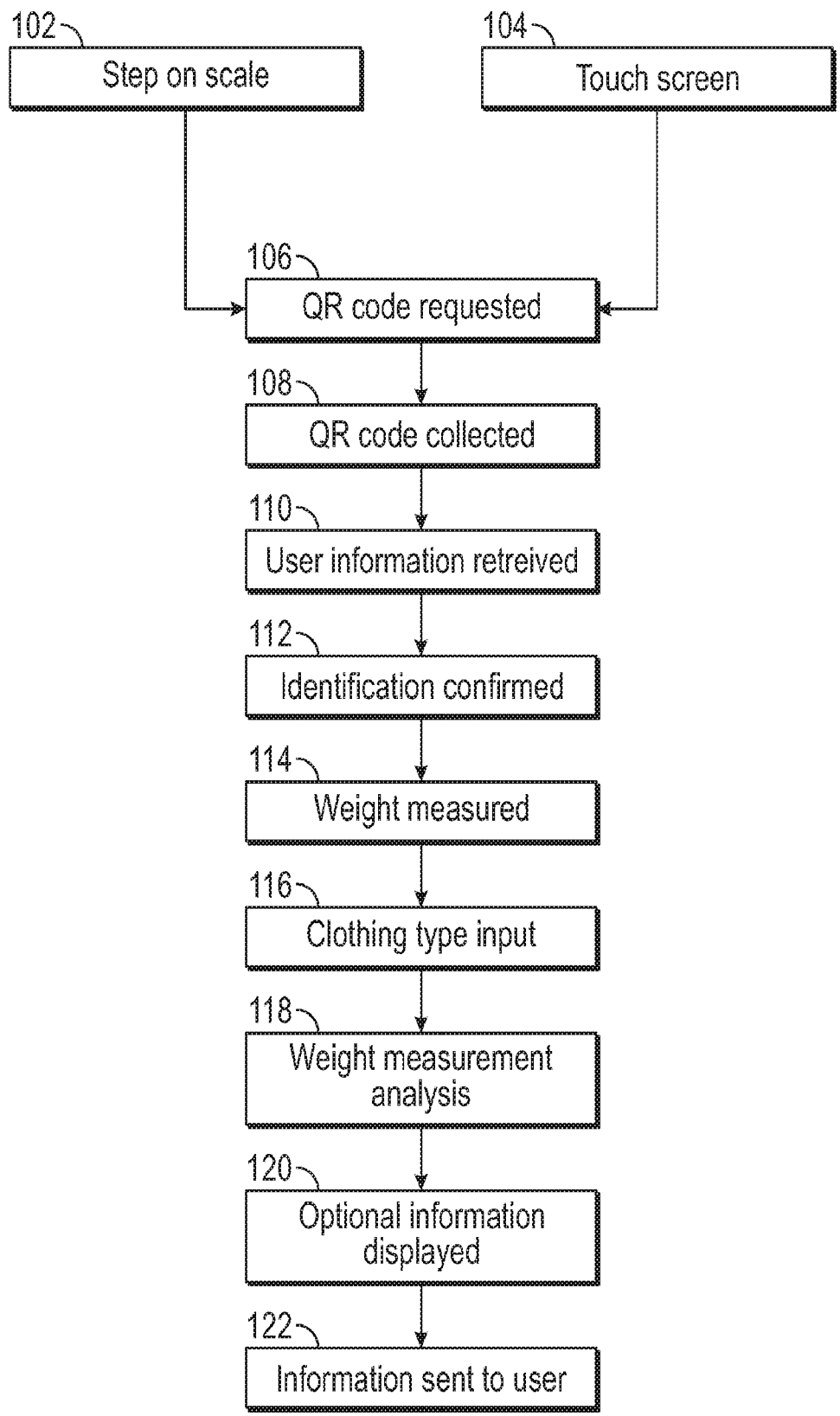
FIG. 5 provides an illustrative flow diagram for weight trend analysis according to an aspect of the application.

Referring now to FIG. 5, a flow diagram showing an exemplary way of collecting data from a user 10 is shown. The process is typically initiated by a user (not shown) stepping onto scale 1110 at 102 or alternatively touching touch screen monitor 1130 at 104. Processing unit 1120 then initializes camera 1140 and a quick response code (commonly called a "OR code") is requested at 106, typically by a request using monitor 1130. The QR code is then collected at 108, typically using camera 1140. Using the QR code, user information is then retrieved at 110. Any other suitable identification information can likewise be used instead of a QR code. Other input devices and methodologies within the scope of the present application can include a mouse, a keyboard, a voice input device, a touch input device for receiving a gesture from a user, a motion input device for detecting non-touch gestures and other motions by a user, and other comparable input devices and associated processing elements capable of receiving user input from a user.

Still referring to FIG. 5, user information is typically retrieved by communicating with a database, such as a database stored on the cloud or other locations, and the user information is then provided to processing unit 1120. Other data retrieval methodologies can likewise be used. Examples of storage media used in connection with the present application include random access memory, read only memory, magnetic discs, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. In some implementations, the storage media can be a non-transitory storage media. In some implementations, at least a portion of the storage media may be transitory.

Still referring to FIG. 5, at 112, the user's identification is confirmed on using monitor 1130. Then, at 114 the user's weight is measured using scale 1110. In one aspect of the application, the user's weight is not displayed. At 116, the user inputs the type of clothing that is being worn by the user by selecting from several options displayed on monitor 1130.

Figure 6:
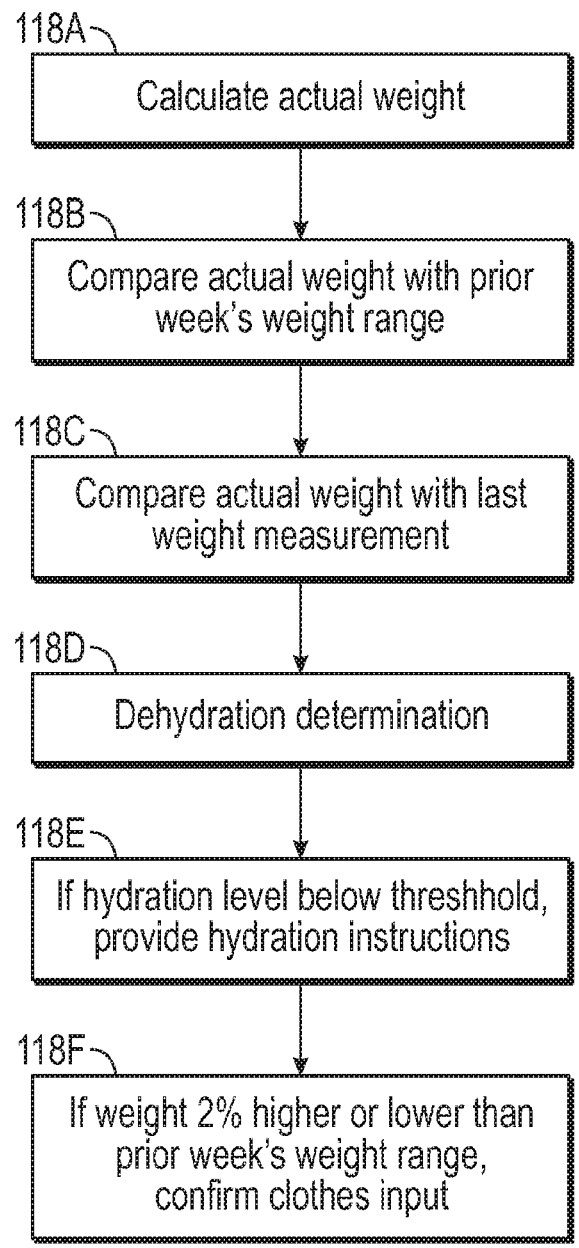
FIG. 6 provides another illustrative flow diagram for weight trend analysis according to another aspect of the application.

Still referring to FIG. 5, at 118 an analysis of the user's weight is performed. This weight analysis is discussed in further detail below and an exemplary, nonlimiting example is provided in FIG. 6. Referring to FIG. 6, at 118A the user's actual weight is calculated by subtracting the clothing weight selected at 116 from the actual weight measured at 114. At 118B, the actual weight calculated in 118A is compared with the prior week's weight range. At 118C, the actual weight is compared with the last weight measurement. At 118D, the system determines whether the user is dehydrated. If the last weight measurement was taken within three (3) hours (or another suitable duration) of the current weight measurement at 114, these two measurements are compared. If the current weight at 114 is more than 300 grams (or another suitable figure) lower than the prior measurement, at 118E information is provided to the user about how much water should be ingested by the user to reach a proper hydration level, and other information can also be provided about proper hydration levels. Referring back to FIG. 5, at 122, the prior week's weight range is compared with the current weight measurement taken at 114. If the current weight is more than two percent (2%) (or another suitable percentage) higher or lower than the prior week's measurement, the user is asked to confirm the weight selection provided at 116.

Referring back to FIG. 5, at 120, optional information such as an advertising message can be displayed using monitor 1130. At 122, a message is displayed on monitor 1130 notifying the user to see the private portion of the application for details regarding the weight analysis. Following is one nonlimiting example of information that can be displayed on monitor 1130 at 122:
"Nice! This is your 4th measurement this week!
It is important to us to build your weekly weight oscillation in order to reveal your future weight trend.
Please see your results on your APP.
Thanks!"

Figure 7:
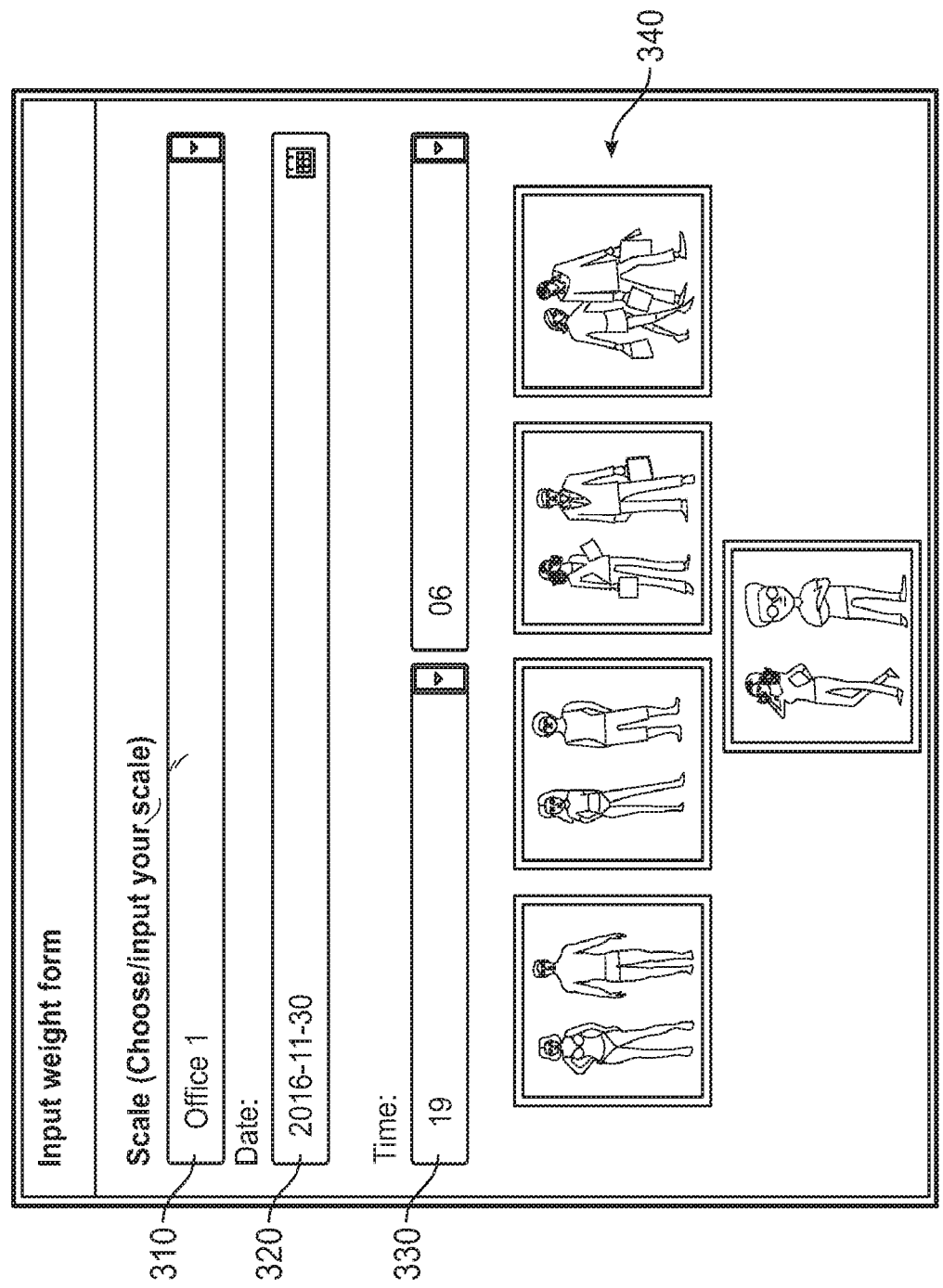
FIG. 7 provides an illustrative user interface for gathering weight information according to another aspect of the application.

In another aspect of the present invention, a user 10 can still utilize the present system when user 10 does not have access to weight tracking station 1100. In such circumstances, user 10 can manually enter the user weight using an app that can be downloaded directly onto user's mobile device such as a smartphone. As yet another alternative, user 10 can also log into a website integrated with the present system to input user's weight. Referring to FIG. 7, an exemplary user interface is shown that can be used to manually enter user's weight using a smart phone device. Here, user 10 will set the device 310 from which user's weight was measured, enter the date 320 and time 330 at which the weight measurement was taken, and select the clothing type 340 worn by user 10 at the time of the weight measurement. This data is then transmitted to subsystem 3000.

As another alternative, a user 10 could take weight measurements using a wi-fi enabled scale that is linked to subsystem 3000 via an Internet connection. After such weight measurement is taken, the user will typically input the same information as described with reference to FIG. 7 except that the user typically will not have to designate the scale device.

The present system typically needs three consecutive weeks of weight measurements in which weight measurement are taken on at least three different days during each week. If one of more of such measurements are not available, the present system can generate a "dummy" or "maintain weight" weight for use in connection with making the calculations and determinations described herein.

3. Weight Oscillation Calculation

Following is an explanation of an exemplary calculation that can be used to determine the weight oscillation of a user. This calculation is for purposes of illustration only and is not intended to limit the present application. This calculation typically uses data that has already been prepared in a database (typically in the cloud), and the algorithm is typically considered an object in the cloud that is separate from the database and used to calculate the weight trend. The information from multiple users can be aggregated in the database and used to prepare collective reports.

3.1 Weight Adjustment

Figure 8:
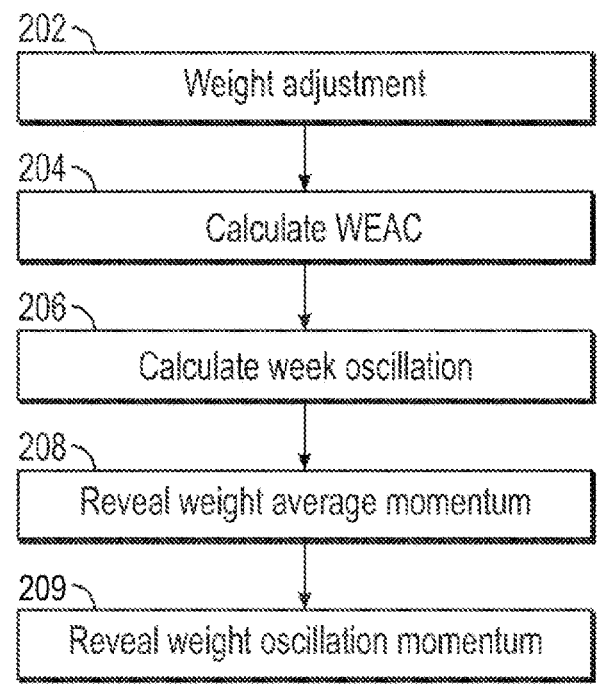
FIG. 8 provides an illustrative flow diagram for an illustrative weight oscillation algorithm according to an aspect of the application.

Referring to FIG. 8, a flow diagram depicts the typical steps of the weight oscillation calculation. At 202, the user weight is adjusted. The following fields are typically populated in the database with information related to each weight measurement:
Weight—"weig"
Date—"date"
Time—"time"
Scale—"scal"
Shoes—"shoe"
Clothes—"clot"
Accessories—"aces"

The weight adjustment is typically calculated by subtracting from the measured weight the sum of shoes, clothes, and accessories, which can be represented by the following formulas.

$$\text{Weight adjusted} = \text{wead}$$

$$\text{Wead} = \text{weig} - (\text{shoe} + \text{clothes} + \text{aces})$$

3.2 Calculating "WEAC"

Still referring to FIG. 8, at 202 the "WEAC" is calculated. "WEAC" is typically a non-actual weight that a first equation (f_Weac) calculates to generate a new "weight" 20 minutes between each actual weight measurements.

$$f\_Weac = \frac{-1*((\text{Time2}*(wead1-wead2))+(wead2*\text{time1})-(wead1*\text{time2})}{(\text{time2}-\text{time1})}$$

Figure 9:
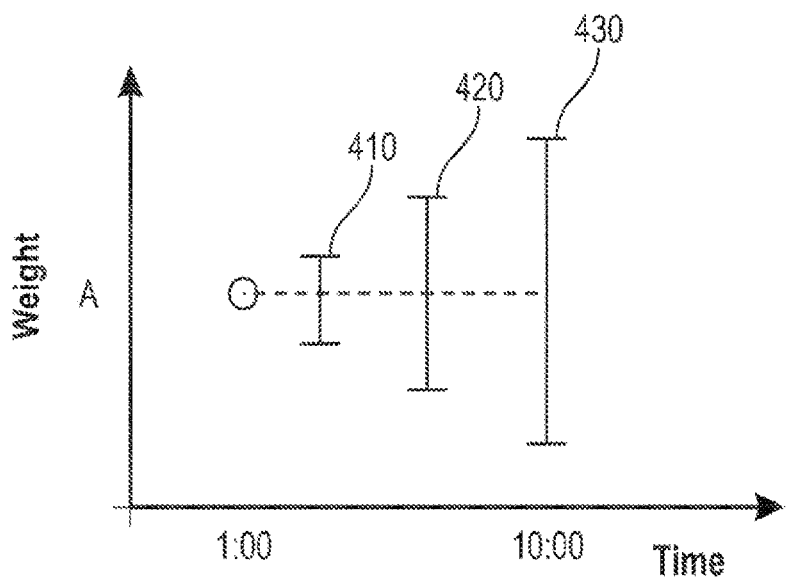
FIG. 9 provides an illustration on weight range measurements taken over time according to aspect of the application.

Referring to FIG. 9, the distance in time between measurements typically can be important because as the time duration between measurements increases, the likelihood of weight oscillation can also increase. Stated another way, as time progresses, the magnitude of weight oscillation such as 410, 420, and 430, can also typically increase as shown in FIG. 9. Following is a brief, nonlimiting explanation for the oscillations shown in FIG. 9. In one aspect, there are typically two groups of "actions" that can impact total human body weight. One group (A) is related to chemical reactions that happens inside our body and are controlled by our metabolism, which include the fat burn process for example, but also includes transpiration. Another group (B) is related to digestive and urological systems, that can accumulate weight by ingest liquids and food and can reduce weight by defecting and urinating. Considering just group A we could understand a slow weight loss between every measurement because our body need to produce energy what consumes water. Theoretically, 15 minutes after of one weight measurement is taken, a second measurement could show a very small total weight reduction, and the total body weight would be lower than the first one. Conversely, it is likewise possible that the second measurement could higher than the first one if the person drank or ate something. The present application typically has a focus on the weekly behavior. Additionally, five hours after one weight measurement, we can have a different weight measurement because of any "action" that results from a group B activity. In contrast to experimental labs, the present application typically includes considerations that just after a weight measurement, a user could go to the bathroom, or even drink water, thereby changing the weight that was just measured.

3.3 Calculating Weekly Oscillation

Referring to FIG. 8, at 206 the weekly weight oscillation is typically calculated. The calculation according to one aspect of the invention typically works with a table that contains two variables: (i) real weight collected by our application (WEAD) and (ii) non-real weight (WEAC), both of which are used to create a table of measurements every week. Starting on Monday 12:20 am and ending on Sunday 11:59 pm. Following is one example of such a table.

| Date/time | Weight |
| --- | --- |
| Time1 | wead1 |
| Time w1 | weac1 |
| Time w2 | weac2 |
| Time w3 | weac3 |
| Time2 | wead2 |
| Time w4 | weac4 |
| Time w5 | weac5 |
| Time w6 | weac6 |
| Time3 | wead3 |

The following equations typically can be used in connection with calculating the weekly oscillation:

Average point=(average of every weight of the week)

STD deviation=Calculation of standard deviation

STD Factor=SDF*STD Deviation

Oscil−=Average point−STD Factor

Oscil+=Average point+STD Factor

The foregoing calculations are based in part upon the observation that that humans typically have a natural total weight oscillation. In connection with this observation, the present application typically does not consider the real, or actual, minimum and maximum values of the weekly weight measurements in connection with analyzing the weekly weight oscillation of a user. Instead, according to aspect of the present application, a standard deviation factor is typically used to improve the accuracy of the model. In one aspect, a standard deviation factor ("SDF") of 2.35781 is used in connection with the present application. In other aspects, this SDF can be less than be less than 4.0, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, and less than 1.0. This SDF is typically multiplied by the standard deviation of a weight data set to produce a "STD Factor," which is used to determine the weekly weight oscillation. The weekly weight oscillation typically is a range of numbers, where the minimum value (Oscil−) is equal to Average point—STD Factor, and the maximum value (Oscil+) is Average point+STD Factor. The present application typically uses this range (i.e., the weight difference between Oscil− and Oscil+) to project the future weight range. The use of this SDF factor can improves the accuracy of the prediction model, potentially by ninety percent (90%) when compared with other methodologies such as those described in the following publications, the contents of which are incorporated herein by reference:

Diana M. Thomas et al., "A Simple Model Predicting Individual Weight Change In Humans," J. Biol. Dyn. 2011 November; 5(6): 579-599, available at www.ncbi.nlm.nih.gov/pmc/articles/PMC3975626/.

LSU Pennington Biomedical Research Center Weight Loss Predictor, available online at www.pbrc.edu/research-and-faculty/calculators/weight-loss-predictor/.

The models and methodologies described in the foregoing resources are complex in comparison to the present application and the accuracy of these resources is related to the user's compliance with the protocol rules. In comparison, the present application is based upon shorter term situations that incorporates "real life" activities into the analysis.

3.4 Determining Weight Average Momentum

Still referring to FIG. 8, at 208 the weight average momentum typically is calculated. The following table identifies the values that are typically calculated using various equations in this step. In one aspect, the present application typically calculates first the "middle" point of the future weight range. After this calculation, referred to as the "AVERAGE," the present application typically calculates the weight range. The minimum value of this range is "Oscil−1" and the maximum point "Oscil+1". As one non-limiting example, assuming the "Actual Week" started on Monday, December 12, "Week-1" would have started on Monday, December 5, and "Week-2" would have started on Monday, November 28.

| | Average | Oscil−1 | Oscil+1 |
| --- | --- | --- | --- |
| Week-2 | AP1 - Average point; It is the average of weight measures of this week. | ON1 - Oscillation Negative; Is equal to the Average Point minus STD Factor of this week | OP1 - Oscillation Positive; Is equal to the Average Point plus STD Factor of this week |
| Week-1 | AP2 - Average point; It is the average of weight measures of this week. | ON2 - Oscillation Negative; Is equal to the Average Point minus STD Factor of this week | OP2 - Oscillation Positive; Is equal to the Average Point plus STD Factor of this week |
| Actual Week | AP3 - Average point; It is the average of weight measures of this week. | ON3 - Oscillation Negative; Is equal to the Average Point minus STD Factor of this week | OP3 - Oscillation Positive; Is equal to the Average Point plus STD Factor of this week |

The following equations are typically applied in this step to determine the weight average momentum.

$Mm32=(AP1+AP2)/2$ $Mm21=(AP2+AP3)/2$ $AV\text{-}2=AP3$ $Week\_f1=(((D9-D8)*4+(D8-((D9-D8)/C16)*2.5)))+D10)/2$ $D9=Mm21; D8=Mm32; C16=wf1adj; D10=AP3$ $Week\_f2=(((D10-d8)*4+(D8-((D10-D8)/C17)*2.5)))+D12)/2$ $D10=AP3; D8=Mm32; C17=wf2adj; D12=Week\_f1$ The equation week_f1 is typically used to find the average number of the weight range at the following week (i.e., the week immediately following the actual week of the current measurement). The week_f2 equation is typically used to find the average number of the weight range at the next following week (i.e., two weeks ahead of the actual week). Using these algorithms, the application is typically capable of determining the users' weight range for the next week after the actual weight measurement and also the second week after the actual weight measurement.

In the above exemplary equation, "wf1adj" is a factor typically used to correct the projection of week 1. It is based on the percentage difference between the average points of week 3 and week 1. This difference is a "key number" that according to one aspect of the application is used for selecting the appropriate factor as shown in the following table that correlates the percentage difference to the appropriate factor. In a similar manner, "wf2adj" is a factor typically used to correct the projection of week 2. It is based on the percentage difference between the average points of week 3 and week 2.

The following tables provide a nonlimiting illustration of determining the "wf1adj" and "wf1adj2" values for use in connection with the application.

| Weight loss speed evaluation | | | |
|---|---|---|---|
| week | average | loss | percent |
| Week −2 | 100.5759 | | |
| Week −1 | 99.51683 | 1.059 | 1.05% |
| Actual Week | 97.81864 | 1.698 | 1.69% |
| AV-4 + AV-2 | | 2.757 | 2.74% |
| | | Wf1adj | 2 |
| week-f1 | 97.037 | 0.782 | 0.79% |
| AV3 + weekf1 | | 2.48 | 2.49% |
| | | Wf2adj | 1.1 |

The below table provides nonlimiting illustrations for the "wf1adj" and "wf2adj" values that correspond to the percent weight loss. For example, in the above table, the week-1 weight loss percent was 2.74%, so the corresponding wf1adj value taken from the below table that corresponds to 2.74% is 2.0.

| References Weight Loss | Wf1adj | | Wf2adj | |
|---|---|---|---|---|
| 5.00% | 2 | 0 | 1 | 0 |
| 4.50% | 2 | 0 | 1 | 0 |
| 4.00% | 2 | 0 | 1.1 | 0 |
| 3.50% | 2 | 0 | 1.1 | 0 |
| 3.00% | 2 | 0 | 1.1 | 0 |
| 2.50% | 2 | 2 | 1.1 | 0 |
| 2.00% | 2 | 0 | 1.1 | 1.1 |
| 1.95% | 2 | 0 | 1.1 | 0 |
| 1.90% | 2 | 0 | 1.1 | 0 |
| 1.85% | 2 | 0 | 1.1 | 0 |
| 1.80% | 2 | 0 | 1.1 | 0 |
| 1.75% | 2 | 0 | 1.1 | 0 |
| 1.70% | 2 | 0 | 1.1 | 0 |
| 1.65% | 2.09 | 0 | 1.1 | 0 |
| 1.60% | 2.17 | 0 | 1.2 | 0 |
| 1.55% | 2.26 | 0 | 1.2 | 0 |
| 1.50% | 2.35 | 0 | 1.2 | 0 |
| 1.45% | 2.44 | 0 | 1.2 | 0 |
| 1.40% | 2.52 | 0 | 1.2 | 0 |
| 1.35% | 2.61 | 0 | 1.2 | 0 |
| 1.30% | 2.7 | 0 | 1.2 | 0 |
| 1.25% | 2.78 | 0 | 1.2 | 0 |
| 1.20% | 2.87 | 0 | 1.2 | 0 |
| 1.15% | 2.96 | 0 | 1.2 | 0 |
| 1.10% | 3.04 | 0 | 1.2 | 0 |
| 1.05% | 2.99 | 0 | 1.2 | 0 |
| 1.00% | 2.99 | 0 | 1.2 | 0 |
| 0.95% | 2.99 | 0 | 1.54 | 0 |
| 0.90% | 2.99 | 0 | 1.54 | 0 |
| 0.85% | 2.99 | 0 | 1.54 | 0 |
| 0.80% | 2.99 | 0 | 1.54 | 0 |
| 0.75% | 2.99 | 0 | 1.54 | 0 |
| 0.70% | 2.99 | 0 | 1.54 | 0 |
| 0.65% | 2.99 | 0 | 1.54 | 0 |
| 0.60% | 2.99 | 0 | 1.54 | 0 |
| 0.55% | 1 | 0 | 1.54 | 0 |
| 0.50% | 1 | 0 | 1.54 | 0 |
| 0.45% | 1 | 0 | 1.54 | 0 |
| 0.40% | 1 | 0 | 1.54 | 0 |
| 0.35% | 1 | 0 | 1.54 | 0 |
| 0.30% | 1 | 0 | 1.54 | 0 |
| 0.25% | 1 | 0 | 1.54 | 0 |
| 0.20% | 1 | 0 | 1.54 | 0 |
| 0.15% | 1 | 0 | 1.54 | 0 |
| 0.10% | 1 | 0 | 1.54 | 0 |
| 0.05% | 1 | 0 | 1.54 | 0 |
| 0.00% | 1 | 0 | 1.54 | 0 |
| −0.05% | 1 | 0 | 0.8 | 0 |
| −0.10% | 1 | 0 | 0.8 | 0 |
| −0.15% | 1 | 0 | 0.8 | 0 |
| −0.20% | 1 | 0 | 0.8 | 0 |
| −0.25% | 1 | 0 | 0.8 | 0 |
| −0.30% | 1 | 0 | 0.8 | 0 |
| −0.35% | 1 | 0 | 0.8 | 0 |
| −0.40% | 1 | 0 | 0.8 | 0 |
| −0.45% | 1 | 0 | 0.8 | 0 |
| −0.50% | 1.023 | 0 | 0.821 | 0 |
| −0.55% | 1.046 | 0 | 0.842 | 0 |
| −0.60% | 1.069 | 0 | 0.863 | 0 |
| −0.65% | 1.092 | 0 | 0.884 | 0 |
| −0.70% | 1.115 | 0 | 0.905 | 0 |
| −0.75% | 1.138 | 0 | 0.926 | 0 |
| −0.80% | 1.161 | 0 | 0.947 | 0 |
| −0.85% | 1.184 | 0 | 0.968 | 0 |
| −0.90% | 1.207 | 0 | 0.989 | 0 |
| −0.95% | 1.23 | 0 | 1.01 | 0 |
| −1.00% | 1.253 | 0 | 1.031 | 0 |
| −1.50% | 1.276 | 0 | 1.052 | 0 |
| −2.00% | 1.299 | 0 | 1.073 | 0 |
| −2.50% | 1.322 | 0 | 1.1 | 0 |
| −3.00% | 1.345 | 0 | 1.1 | 0 |
| −3.50% | 1.368 | 0 | 1.1 | 0 |
| −4.00% | 1.391 | 0 | 1.1 | 0 |
| −4.50% | 1.414 | 0 | 1.1 | 0 |
| −5.00% | 1.437 | 0 | 1.1 | 0 |

3.5 Determining Weight Oscillation Momentum

Still referring to FIG. 8, at 209 the weight oscillation momentum typically is determined. The following equations are typically used in connection with making this determination.

$$\text{Oscillation-week}\_f1 = D12 - (0.6 * \text{average}(\text{difofOscil}))$$

$$\text{Oscillation-week}\_f2 = \text{week}\_f1 + (0.6 * (((OP1-ON1) + (OP2-ON2) \pm (OP3-ON3))/3)$$

As explained above, an aspect of the present application is the calculation of the weekly weight ranges for a user. The equations "Oscillation-week_f1" and "Oscillation-week_f2" typically complement the "week_f1" and "week_f2" equations explained above in order to generate the future two week weight range (weight range for the first week after the week of the actual measurement, and the to the second week after the week of the actual measurement.)

The week-f1 and week-f2 equations typically result from the average point of the future weights of the "next," or subsequent, two weeks after week 3, which could otherwise be referred to as week4 and week5. In one aspect, the present application uses "week-f1" for week 4 and "week-f2" for week 5. To calculate the weight ranges "around" these average points, the present application typically calculates the "size" of the oscillation. The calculations for "Oscillation-week_f1" and "Oscillation-week_f2" are typically used to determine this oscillation. The following equations are typically used in connection with these determination.

- the minimum point of the oscillation-week_f1 is equal to {D12–[0.6*(average of the last three weekly oscillations)]};
- the maximum point of the oscillation-week_f1 is equal to {D12+[0.6*(average of the last three weekly oscillations)]};
- the minimum point of the oscillation-week_f2 is equal to {D13–[0.6*(average of the last three weekly oscillation)]};
- the maximum point of the oscillation-week_f2 is equal to {D13+[0.6*(average of the last three weekly oscillation)]}

D13 is equal to the week-f2 calculation explained above; "average of the last three weekly oscillations" (also referred to as "average(difofOscil)")=(((OP1−ON1)+(OP2−ON2)+(OP3−ON3))/3)

Figure 10:
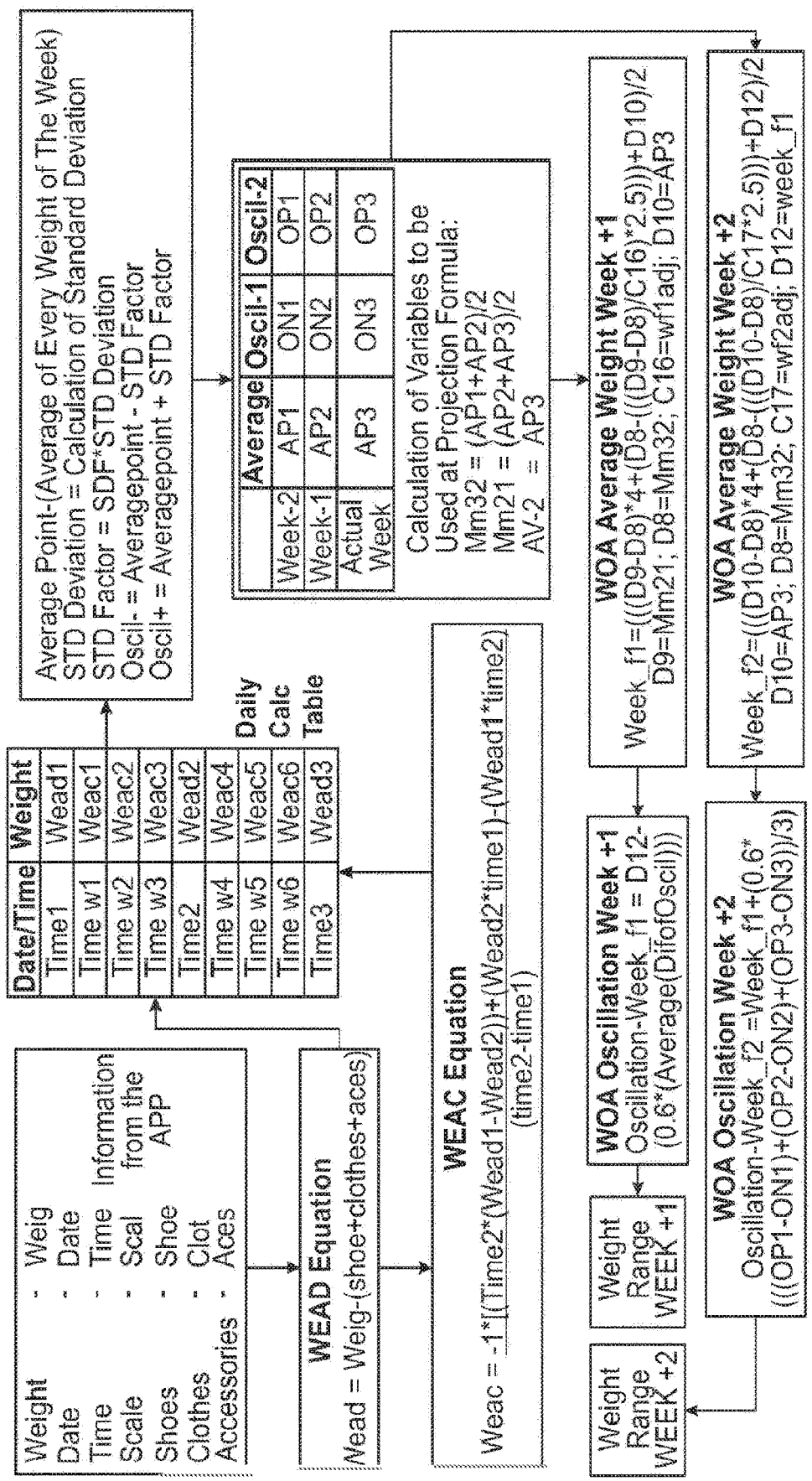
FIG. 10 provides another illustrative flow diagram for an illustrative weight oscillation algorithm according to an aspect of the application.
Figure 11:
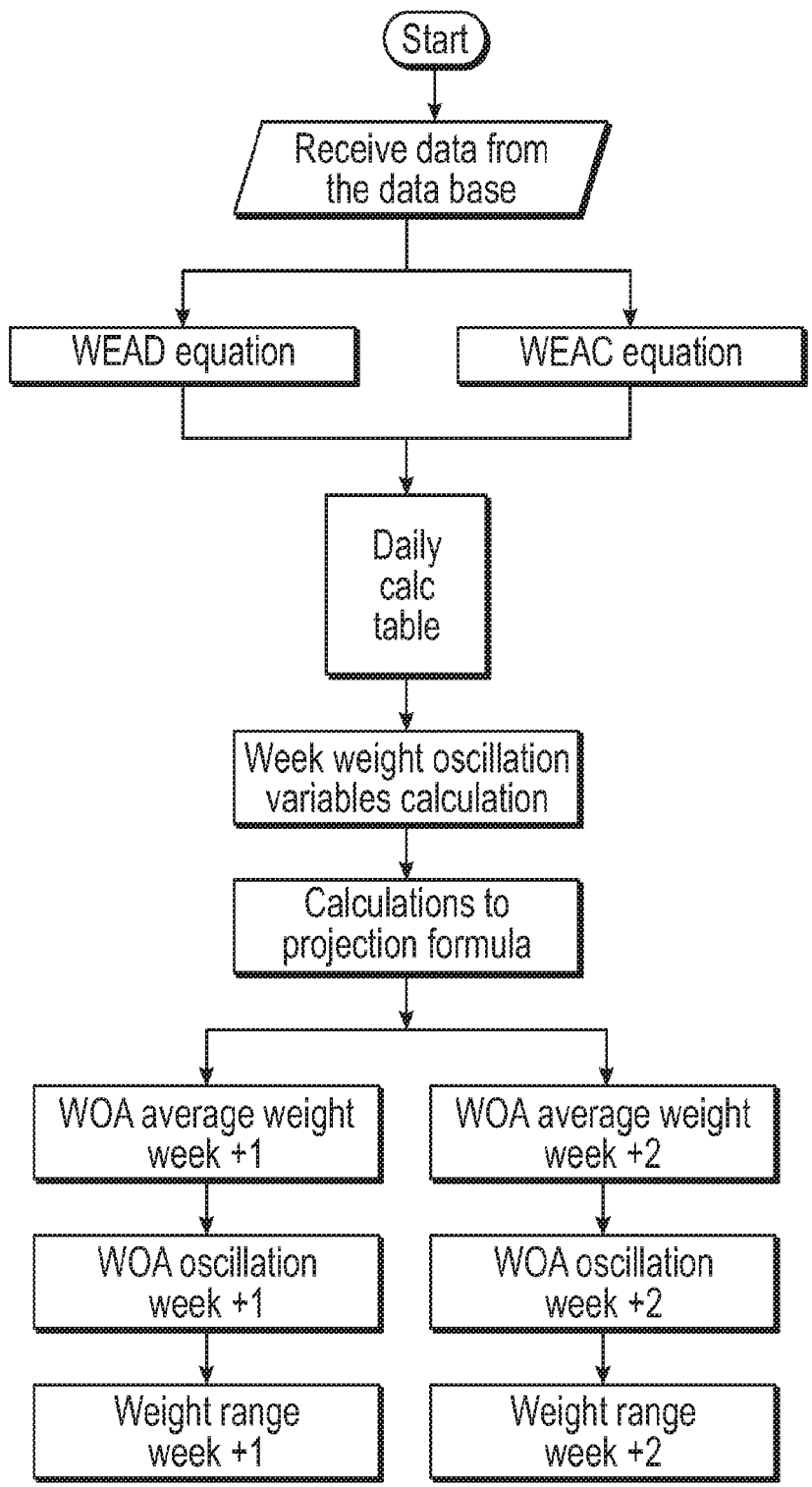
FIG. 11 provides another illustrative flow diagram for an illustrative weight oscillation algorithm according to an aspect of the application.

Referring to FIGS. 10 and 11, flow diagrams providing additional context for the foregoing equations are provided.

4. Information Delivery

In another aspect of the application, information is typically provided to a user that is intended to assist the user in understanding and monitoring the user's weight trend and weight oscillation, which can be useful in managing the user's weight loss goals. In order to accomplish this, the present application typically tracks a periodic (e.g., weekly) weight range rather than tracking a specific weight number. The present application typically includes an interface that permits user to see the user's predicted weight range two weeks in advance and also typically notifies a user if the pace of user's weight gain or loss is adequate to meet the user's desired outcome, such as losing weight or gaining weight.

Figure 12:
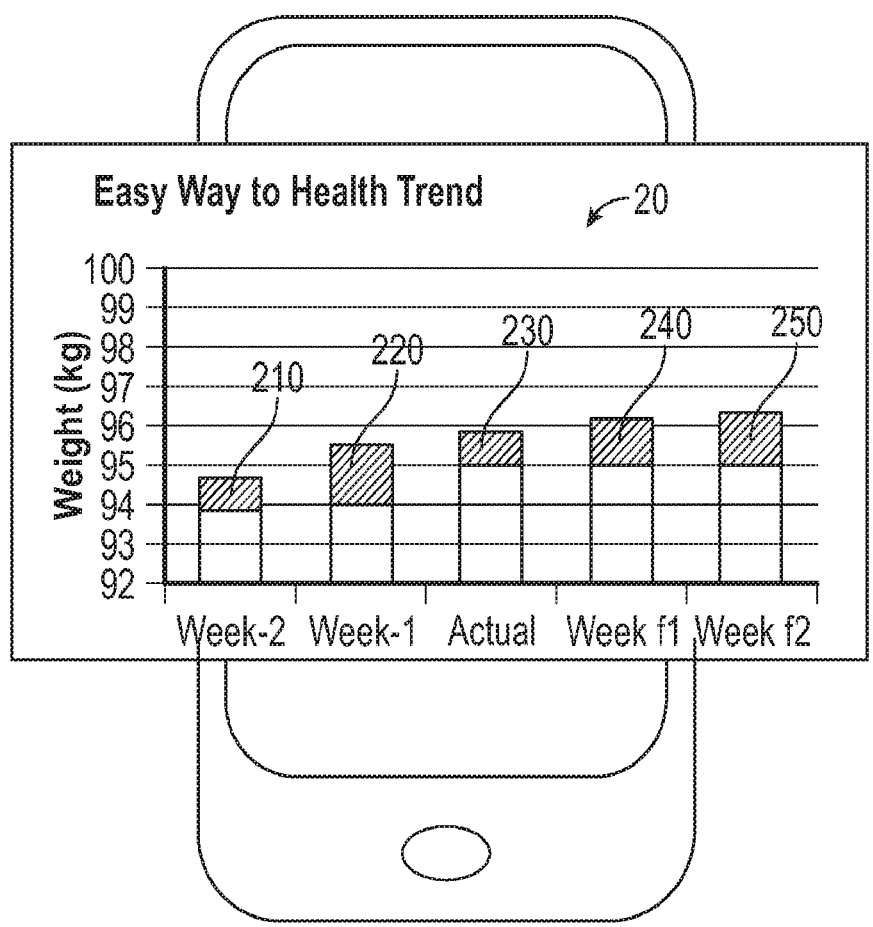
FIG. 12 provides an illustration of weight trend output according to an aspect of the application.

Referring to FIG. 12, according to another aspect of the invention, output typically is shown on the display of a mobile device 20 such as a smartphone. The weight trend shown is a graphic visualization of the weekly weight range for the current (or actual) week 230, the weekly weight range for one week prior 220 and two weeks prior 210, as well as for one week in the future 240 and two weeks in the future 250.

Figure 13:
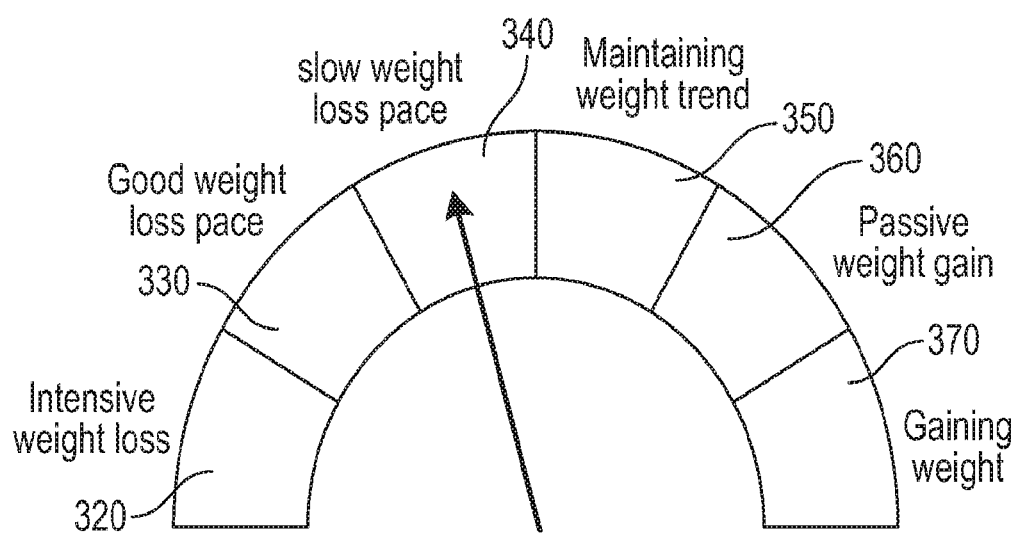
FIG. 13 provides another illustration of weight trend output according to an aspect of the application.

Referring to FIG. 13, another output 300 according to an aspect of the invention is shown. Here, a virtual needle, or pointer, 310 typically designates the portion of a scale corresponding to the user's weight loss trend. For example, needle 310 will point to portion 320 when the user is experiencing intense weight loss. In such circumstances, the user should attempt to reduce the pace at which weight is being lost. As another example, needle 310 will point to portion 330 when the user is experiencing a good weight loss pace. This signifies that the user should continue following the same behaviors and activities to continue losing weight on a good pace. Such a "good" pace typically prevents a user from hitting a "plateau" situation in which weight loss is typically stunted. Such plateaus can result in users losing motivation to stay on a weight loss program. Any other suitable display methodology can also be used to convey the weight loss or weight gain trend information to a user.

Still referring to FIG. 13, needle 310 typically will point to portion 340 when user is on a slow weight loss pace, and point to portion 350 when user is maintaining the same weight loss trending. Needle 310 will point to portion 360 when the user is experiencing a passive weight gain pace, and to portion 340 when the user is gaining weight. The calculations used to determine the weight loss trend are typically based upon the week three weight range and week five weight range. As previously explained, the present application typically expresses the "distance" between the actual weight range (week3, or the present week) and the future weight range two weeks out (also referred to herein as week5 or "week_f2"). For example, if the week-f2 has a weight range that has a maximum oscillation that is lower than the maximum oscillation for week 3, the user of the present application would typically be losing weight. If such weight loss is greater than three percent (3%), the user is typically losing weight at a more rapid pace than desired, which can result in non-sustainable weight loss.

Figure 14:
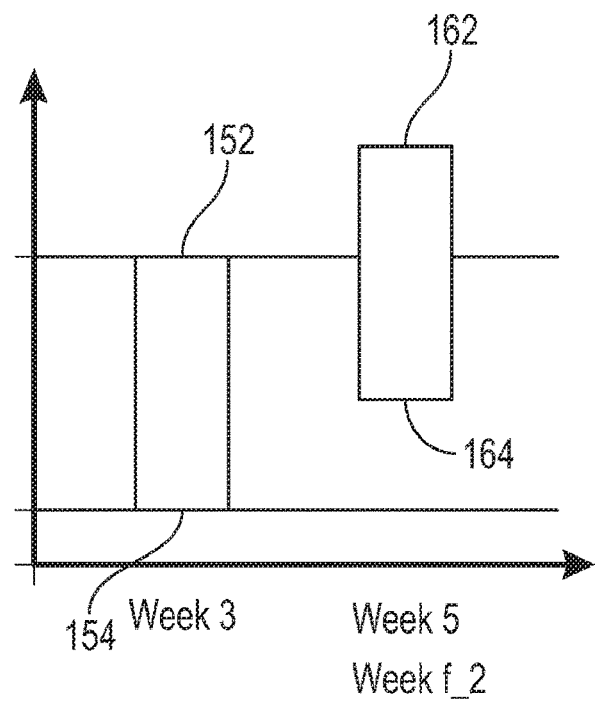
FIG. 14 provides an illustration of weekly weight oscillation trends determined according to an aspect of the application.

Referring to FIG. 14, an illustrative, nonlimiting example of a user's weekly weight oscillation for week 3 and week 5 are shown. The maximum oscillation value for the week 3 range is shown at 152, and the minimum oscillation value for the week 3 range is shown at 154. The maximum oscillation value for the for week 5 range is shown at 156, and the minimum oscillation value for the for week 5 range is shown at 164. As described above, week 5 is also referred to herein as "week-f2". Also as previously explained, the present application uses the difference between the maximum value of the weight range (e.g., maximum oscillation−Oscil+1) as a factor when determining the weight loss trend. The following table provides an example of the weight oscillation calculations that correspond to the weight trend category typically displayed to the user.

| Category | Calculation (The maximum point of the oscillation-week_f2 − maximum point of oscillation week 3) |
|---|---|
| Gaining Weight | If the result is positive and bigger than 1% of the maximum point of the oscillation-week_f2 |
| Slow gain weight/ Passive weight gain | If the result is positive but smaller than 1% of the maximum point of the oscillation-week_f2 |

| Category | Calculation (The maximum point of the oscillation-week_f2 − maximum point of oscillation week 3) |
|---|---|
| Maintaining weight trend | If the result is positive but smaller than 0.5% or negative but higher than 0.5% of the maximum point of the oscillation-week_f2 |
| Slow weight loss pace | If the result is negative but lower than 1% of the maximum point of the oscillation-week_f2 |
| Good weight loss pace | If the result is negative but lower than 2.3% of the maximum point of the oscillation-week_f2 |
| Invasive weight loss | If the result is negative but higher than 2.3% of the maximum point of the oscillation-week_f2 |

Again referring to FIG. 14, as illustrated the week 5 (or "week f_2") maximum oscillation point 162 is greater than the week 3 maximum 152, so the present application treats the user as having gained weight. Because the week 5 maximum oscillation value 162 is more than one percent of the week three (or "week_f1"), the user is treated as having gained weight according to the present application, and the needle of FIG. 13 will point to portion 340 when the user is gaining weight.

5. Use Example

Figure 15:
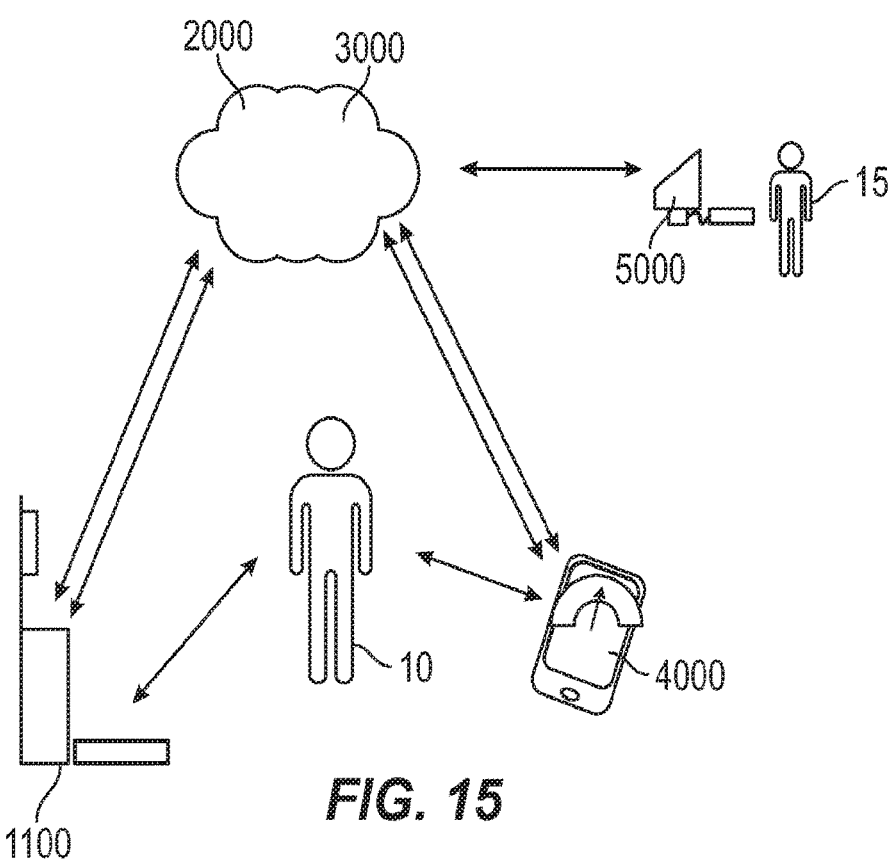
FIG. 15 provides an illustration of a weight measure system according to an aspect of the application.

With reference to FIG. 15, an illustration of the typically overall use of the present system according to an aspect of the application is provided. This illustration is by way of example only and is not intended to limit the scope of the present application. A user 10 will typically step onto the scale 1110 of weight tracking station 1100. The weight measurement and other data collected from user 10 are typically transmitted and stored in a remote database 2000 (see FIG. 3), typically in the cloud. The resulting information calculated according to the weight trend and oscillation equations described herein are then transmitted to an app that has been downloaded on a mobile device 4000 that belongs to 10. The information provided to user 10 typically notifies user about the weight loss trend of user 10 and whether such trend is occurring at an appropriate pace. User 10 also can obtain weight trend and other information by logging into the present system using a computer 5000 that is connected to the Internet. Computer 5000 can also typically be used to maintain the overall system by another user such as a system administrator 15 or other person. All of the information collected about the user, as well as all of the calculations and determinations concerning the user, can likewise optionally be shared with others such as healthcare providers, insurance companies, and any other desired entity.

In another aspect, statistics about weight trend and the BMI for a group of users can be shared with corporate users such as businesses, fitness centers, and healthcare facilities. Such statistics can be used to assist in tracking and monitoring the overall weight trends for different groups of people.

The functional block diagrams, operational sequences, calculations, and flow diagrams provided in the figures and throughout this application are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for computerized generation of weight oscillation and weight trends, comprising:
 obtaining a plurality of outputs from a weight acquisition element to a computer processing device, wherein the weight acquisition element does not directly or indirectly convey an acquired weight measurement to a user being weighed on the weight acquisition element, further wherein the computer processing device operates in accordance with an algorithm included within an operating instruction set to store the plurality of outputs in a weight database as current weight measurements, wherein the computer processing device includes a data acquisition processor, a data storage processor, a data processing processor, and an information delivery processor;
 receiving a plurality of current weight measurements over a period of time for the user by the data acquisition processor;
 receiving a set of clothing information about clothing worn by the user at a time of each of the plurality of current weight measurements by the data acquisition processor;
 for each of the plurality of current weight measurements, generating an actual weight measurement based on the current weight measurement and the clothing associated with the current weight measurement, by the data processing processor;
 storing each of the plurality of current weight measurements as a weight data structure, the weight data structure including fields for the current weight measurement, the set of clothing information associated with the current weight measurement, a date of the current weight measurement, the time of the current weight measurement, and the actual weight measurement;
 receiving, by the data processing processor, from a data storage processor a plurality of weight data structures for a week one time period;
 generating, by the data processing processor, an oscillation prediction model based on the plurality of weight data structures for the week one time period;
 predicting, by the data processing processor, a plurality of predicted weight values for each of a plurality of intervals between each weight data structure for the week one time period with the oscillation prediction model;

updating, by the data processing processor, the oscillation prediction model based on the plurality of predicted weight values for the week one time period;

generating, by the data processing processor, a week one oscillation range using the oscillation prediction model and the plurality of predicted weight values for the week one time period;

receiving, by the data processing processor, from the data storage processor a plurality of weight data structures for a week two time period;

updating, by the data processing processor, the oscillation prediction model based on the plurality of weight data structures for the week two time period;

predicting, by the data processing processor, a plurality of predicted weight values for each of a plurality of intervals between each weight data structure for the week two time period using the oscillation prediction model;

updating, by the data processing processor, the oscillation prediction model based on the plurality of predicted weight values for the week two time period;

generating, by the data processing processor, a week two oscillation range using the oscillation prediction model and the plurality of predicted weight values for week two;

receiving, by the data processing processor, from the data storage processor a plurality of weight data structures for a week three time period;

updating, by the data processing processor, the oscillation prediction model based on the plurality of weight data structures for the week three time period;

predicting, by the data processing processor, a plurality of predicted weight values for each of a plurality of intervals between each weight data structure for the week three time period using the oscillation prediction model;

updating, by the data processing processor, the oscillation prediction model based on the plurality of predicted weight values for the week three time period;

generating, by the data processing processor, a week three oscillation range using the oscillation prediction model and the plurality of predicted weight values for the week three time period;

wherein the week one time period, the week two time period, and the week three time period are consecutively occurring weeks, further wherein the week three time period is a current week, the week two time period is a first previous week, and the week one time period is a second previous week, wherein the week one oscillation range, the week two oscillation range, and the week three oscillation range each include an average weight point, a positive oscillation, and a negative oscillation associated with each respective week, further wherein the oscillation prediction model is continually and consecutively updated;

generating, by the data processing processor, a predicted weight average momentum for a week four time period and a week five time period, wherein the week four time period and the week five time period are consecutively occurring weeks to the week one time period, the week two time period, and the week three time period, further wherein the week four time period is a first future week and the week five time period is a second future week, the weight average momentum generating includes:

generating a weight difference percentage for each of the week one time period, the week two time period and the week three time period;

accessing an adjustment factor table from stored media to determine a week one adjustment factor and a week two adjustment factor based on the weight difference percentages generated;

generating a predicted average weight range for each of the week four time period and the week five time period based on the average weight points for the week one time period, the week two time period and the week three time period, the week one adjustment factor, and the week two adjustment factor;

generating a predicted weight oscillation momentum for each of the week four time period and the week five time period based on the oscillation prediction model;

converting, by the data processing processor, the weight average momentum for each of the week four time period and the week five time period to a weight trend; and displaying, by the information delivery processor, the weight trend and the weight average momentum for each of the week four time period and the week five time period on a graphical user interface of an application on a user device of the user by an information delivery processor, wherein the weight trend is a graphical representation of a visual comparison between the weight average momentum for each of the week four time period and the week five time period and the week one oscillation range, the week two oscillation range, and the week three oscillation range.

2. The method of claim 1, further comprising receiving identification information specific to the user prior to receiving each of the plurality of current weight measurements.

3. The method of claim 1, further comprising determining a hydration level of the user if any of the plurality of current weight measurements were collected within a predetermined timeframe.

4. The method of claim 3, wherein the predetermined timeframe is three hours.

5. The method of claim 1, wherein each interval of the plurality of intervals for the predicted weights are twenty minute intervals.

6. The method of claim 1, further comprising:
comparing a most recent current weight measurement to a prior week's weight oscillation range;
instructing the user to collect a second current weight measurement when the most recent current weight measurement is outside of a threshold range or the prior week's weight oscillation range.

7. A system for weight management, comprising:
a graphical user interface on a user device for receiving information from a user and displaying weight trends and weight average momentums;
a computer processing device, the computer processing device including:
a memory comprising computer readable instructions; and
a data acquisition processor, a data storage processor, a data processing processor, and an information delivery processor, each configured to reach the computer readable instructions that when executed causes the system to:

obtain a plurality of outputs from a weight acquisition element to the computer processing device, wherein the weight acquisition element does not directly or indirectly convey an acquired weight measurement to the user being weighed on the weight acquisition element, further wherein the computer processing device operates in accordance with an algorithm included within an operating instruction set to store the plurality of outputs in a weight database as current weight measurements;

receive a plurality of current weight measurements over a period of time for the user by the data acquisition processor;

receive a set of clothing information about clothing worn by the user at a time of each of the plurality of current weight measurements by the data acquisition processor;

for each of the plurality of current weight measurements, generate an actual weight measurement based on the current weight measurement and the clothing associated with the current weight measurement, by the data processing processor;

store each of the plurality of current weight measurements as a weight data structure, the weight data structure including fields for the current weight measurement, the set of clothing information associated with the current weight measurement, a date of the current weight measurement, the time of the current weight measurement, and the actual weight measurement;

receive, by the data processing processor, from a data storage processor a plurality of weight data structures for a week one time period;

generate, by the data processing processor, an oscillation prediction model based on the plurality of weight data structures for the week one time period;

predict, by the data processing processor, a plurality of predicted weight values for each of a plurality of intervals between each weight data structure for the week one time period with the oscillation prediction model;

update, by the data processing processor, the oscillation prediction model based on the plurality of predicted weight values for the week one time period;

generate, by the data processing processor, a week one oscillation range using the oscillation prediction model and the plurality of predicted weight values for the week one time period;

receive, by the data processing processor, from the data storage processor a plurality of weight data structures for a week two time period;

update, by the data processing processor, the oscillation prediction model based on the plurality of weight data structures for the week two time period;

predict, by the data processing processor, a plurality of predicted weight values for each of a plurality of intervals between each weight data structure for the week two time period using the oscillation prediction model;

update, by the data processing processor, the oscillation prediction model based on the plurality of predicted weight values for the week two time period;

generate, by the data processing processor, a week two oscillation range using the oscillation prediction model and the plurality of predicted weight values for week two;

receive, by the data processing processor, from the data storage processor a plurality of weight data structures for a week three time period:

update, by the data processing processor, the oscillation prediction model based on the plurality of weight data structures for the week three time period;

predict, by the data processing processor, a plurality of predicted weight values for each of a plurality of intervals between each weight data structure for the week three time period using the oscillation prediction model;

update, by the data processing processor, the oscillation prediction model based on the plurality of predicted weight values for the week three time period;

generate, by the data processing processor, a week three oscillation range using the oscillation prediction model and the plurality of predicted weight values for the week three time period;

wherein the week one time period, the week two time period, and the week three time period are consecutively occurring weeks, further wherein the week three time period is a current week, the week two time period is a first previous week, and the week one time period is a second previous week, wherein the week one oscillation range, the week two oscillation range, and the week three oscillation range each includes an average weight point, a positive oscillation, and a negative oscillation associated with each respective week, further wherein the oscillation prediction model is continually and consecutively updated;

generate, by the data processing processor, a predicted weight average momentum for a week four time period and a week five time period, wherein the week four time period and the week five time period are consecutively occurring weeks to the week one time period, the week two time period, and the week three time period, further wherein the week four time period is a first future week and the week five time period is a second future week, the weight average momentum generating includes:

generate a weight difference percentage for each of the week one time period, the week two time period and the week three time period;

access an adjustment factor table from stored media to determine a week one adjustment factor and a week two adjustment factor based on the weight difference percentages generated;

generate a predicted average weight range for each of the week four time period and the week five time period based on the average weight points for the week one time period, the week two time period and the week three time period, the week one adjustment factor, and the week two adjustment factor; and generate a predicted weight oscillation momentum for each of the week four time period and the week five time period based on the oscillation prediction model;

convert, by the data processing processor, the weight average momentum for each of the week four time period and the week five time period to a weight trend; and display, by the information delivery processor, the weight trend and the weight average momentum for each of the week four time period and the week five time period on a graphical user interface of an application on a user device of the user by an information delivery processor, wherein the weight trend is a graphical representation of a visual comparison between the weight average momentum for each of the week four time period and the week five time period and the week one oscillation range, the week two oscillation range, and the week three oscillation range.

8. The system of claim 7, wherein the system is further caused to receive identification information specific to the user prior to receiving each of the plurality of current weight measurements.

9. The method of claim 7, wherein the system is further caused to determine a hydration level of the user if any of the plurality of current weight measurements were collected within a predetermined timeframe.

10. The method of claim 9, wherein the predetermined timeframe is three hours.

11. The method of claim 7, wherein each interval of the plurality of intervals for the predicted weights are twenty minute intervals.

12. The method of claim 7, wherein the system is further caused to:
  compare a most recent current weight measurement to a prior week's weight oscillation range;
  instruct the user to collect a second current weight measurement when the most recent current weight measurement is outside of a threshold range or the prior week's weight oscillation range.

13. A non-transitory computer readable medium comprising computer readable code to generate of weight oscillation and weight trends on a system that when executed by a processor, causes the system to:
  obtain a plurality of outputs from a weight acquisition element to a computer processing device, wherein the weight acquisition element does not directly or indirectly convey an acquired weight measurement to a user being weighed on the weight acquisition element, further wherein the computer processing device operates in accordance with an algorithm included within an operating instruction set to store the plurality of outputs in a weight database as current weight measurements, wherein the computer processing device includes a data acquisition processor, a data storage processor, a data processing processor, and an information delivery processor;
  receive a plurality of current weight measurements over a period of time for the user by the data acquisition processor;
  receive a set of clothing information about clothing worn by the user at a time of each of the plurality of current weight measurements by the data acquisition processor;
  for each of the plurality of current weight measurements, generate an actual weight measurement based on the current weight measurement and the clothing associated with the current weight measurement, by the data processing processor;
  store each of the plurality of current weight measurements as a weight data structure, the weight data structure including fields for the current weight measurement, the set of clothing information associated with the current weight measurement, a date of the current weight measurement, the time of the current weight measurement, and the actual weight measurement;
  receive, by the data processing processor, from a data storage processor a plurality of weight data structures for a week one time period;
  generate, by the data processing processor, an oscillation prediction model based on the plurality of weight data structures for the week one time period;
  predict, by the data processing processor, a plurality of predicted weight values for each of a plurality of intervals between each weight data structure for the week one time period with the oscillation prediction model;
  update, by the data processing processor, the oscillation prediction model based on the plurality of predicted weight values for the week one time period;
  generate, by the data processing processor, a week one oscillation range using the oscillation prediction model and the plurality of predicted weight values for the week one time period;
  receive, by the data processing processor, from the data storage processor a plurality of weight data structures for a week two time period;
  update, by the data processing processor, the oscillation prediction model based on the plurality of weight data structures for the week two time period;
  predict, by the data processing processor, a plurality of predicted weight values for each of a plurality of intervals between each weight data structure for the week two time period using the oscillation prediction model;
  update, by the data processing processor, the oscillation prediction model based on the plurality of predicted weight values for the week two time period;
  generate, by the data processing processor, a week two oscillation range using the oscillation prediction model and the plurality of predicted weight values for week two;
  receive, by the data processing processor, from the data storage processor a plurality of weight data structures for a week three time period;
  update, by the data processing processor, the oscillation prediction model based on the plurality of weight data structures for the week three time period;
  predict, by the data processing processor, a plurality of predicted weight values for each of a plurality of intervals between each weight data structure for the week three time period using the oscillation prediction model;
  update, by the data processing processor, the oscillation prediction model based on the plurality of predicted weight values for the week three time period;
  generate, by the data processing processor, a week three oscillation range using the oscillation prediction model and the plurality of predicted weight values for the week three time period;
  wherein the week one time period, the week two time period, and the week three time period are consecutively occurring weeks, further wherein the week three time period is a current week, the week two time period is a first previous week, and the week one time period is a second previous week, wherein the week one oscillation range, the week two oscillation range, and the week three oscillation range each includes an average weight point, a positive oscillation, and a negative oscillation associated with each respective week, further wherein the oscillation prediction model is continually and consecutively updated;
  generate, by the data processing processor, a predicted weight average momentum for a week four time period and a week five time period, wherein the week four time period and the week five time period are consecutively occurring weeks to the week one time period, the week two time period, and the week three time period, further wherein the week four time period is a first future week and the week five time period is a second future week, the weight average momentum generating includes:
generating a weight difference percentage for each of the week one time period, the week two time period and the week three time period;
access an adjustment factor table from stored media to determine a week one adjustment factor and a week two adjustment factor based on the weight difference percentages generated;
generate a predicted average weight range for each of the week four time period and the week five time period based on the average weight points for the week one time period, the week two time period and the week three time period, the week one adjustment factor, and the week two adjustment factor; and
generate a predicted weight oscillation momentum for each of the week four time period and the week five time period based on the oscillation prediction model;
convert, by the data processing processor, the weight average momentum for each of the week four time period and the week five time period to a weight trend; and
display, by the information delivery processor, the weight trend and the weight average momentum for each of the week four time period and the week five time period on a graphical user interface of an application on a user device of the user by an information delivery processor, wherein the weight trend is a graphical representation of a visual comparison between the weight average momentum for each of the week four time period and the week five time period and the week one oscillation range, the week two oscillation range, and the week three oscillation range.

14. The non-transitory computer readable medium of claim 13, wherein the system is further caused to receive identification information specific to the user prior to receiving each of the plurality of current weight measurements.

15. The non-transitory computer readable medium of claim 13, wherein the system is further caused to determine a hydration level of the user if any of the plurality of current weight measurements were collected within a predetermined timeframe.

16. The non-transitory computer readable medium of claim 15, wherein the predetermined timeframe is three hours.

17. The non-transitory computer readable medium of claim 13, wherein each interval of the plurality of intervals for the predicted weights are twenty minute intervals.

18. The non-transitory computer readable medium of claim 13, wherein the system is further caused to:
compare a most recent current weight measurement to a prior week's weight oscillation range;
instruct the user to collect a second current weight measurement when the most recent current weight measurement is outside of a threshold range or the prior week's weight oscillation range.

* * * * *